United States Patent
Gotoh et al.

(10) Patent No.: US 11,464,786 B2
(45) Date of Patent: Oct. 11, 2022

(54) CXCR7 INHIBITORS FOR THE TREATMENT OF CANCER

(71) Applicant: CHEMOCENTRYX, INC., San Carlos, CA (US)

(72) Inventors: Noriko Gotoh, Kanazawa (JP); James J. Campbell, San Jose, CA (US)

(73) Assignee: ChemoCentryx, Inc., San Carlos, CA (US)

( * ) Notice: Subject to any disclaimer, the term of this patent is extended or adjusted under 35 U.S.C. 154(b) by 0 days.

(21) Appl. No.: 16/710,160

(22) Filed: Dec. 11, 2019

(65) Prior Publication Data

US 2020/0188410 A1 Jun. 18, 2020

Related U.S. Application Data

(60) Provisional application No. 62/778,605, filed on Dec. 12, 2018.

(51) Int. Cl.
| | |
|---|---|
| *A61K 31/551* | (2006.01) |
| *A61K 31/395* | (2006.01) |
| *C07K 16/22* | (2006.01) |
| *A61P 35/00* | (2006.01) |
| *A61K 39/395* | (2006.01) |
| *A61K 31/4985* | (2006.01) |

(52) U.S. Cl.
CPC ........ *A61K 31/551* (2013.01); *A61K 31/4985* (2013.01); *A61K 39/3955* (2013.01); *A61P 35/00* (2018.01)

(58) Field of Classification Search
CPC ............ A61K 2039/505; A61K 31/551; A61K 31/4918; A61K 31/4989; A61K 31/395; A61K 39/3955; A61K 2300/00; C07K 2317/71; C07K 16/22; A61P 35/00
See application file for complete search history.

(56) References Cited

U.S. PATENT DOCUMENTS

| | | | |
|---|---|---|---|
| 3,920,636 A | 11/1975 | Takahashi et al. | |
| 6,225,312 B1 | 5/2001 | Feenstra et al. | |
| 7,557,213 B2 | 7/2009 | Melikian et al. | |
| 8,288,373 B2 | 10/2012 | Chen et al. | |
| 8,853,202 B2 | 10/2014 | Chen et al. | |
| 9,169,261 B2 | 10/2015 | Fan et al. | |
| 9,670,212 B2 * | 6/2017 | Leahy | C07D 413/14 |
| 9,783,544 B2 | 10/2017 | Fan et al. | |
| 11,059,825 B2 | 7/2021 | Fan et al. | |
| 2005/0043367 A1 | 2/2005 | Bridger et al. | |
| 2005/0074826 A1 | 4/2005 | Burns et al. | |
| 2005/0214287 A1 | 9/2005 | Burns et al. | |
| 2005/0244408 A1 | 11/2005 | Cohen et al. | |
| 2005/0281812 A1 | 12/2005 | Cohen et al. | |
| 2006/0069102 A1 | 3/2006 | Leban et al. | |
| 2006/0074071 A1 | 4/2006 | Melikian et al. | |
| 2006/0247253 A1 | 11/2006 | Leban et al. | |
| 2007/0021484 A1 | 1/2007 | Melikian et al. | |
| 2007/0167443 A1 | 7/2007 | Melikian et al. | |
| 2007/0254886 A1 | 11/2007 | Habashita et al. | |
| 2007/0254915 A1 | 11/2007 | Leleti et al. | |
| 2007/0275965 A1 | 11/2007 | Thomas et al. | |
| 2008/0161278 A1 | 7/2008 | Thomas et al. | |
| 2009/0022717 A1 | 1/2009 | Premack et al. | |
| 2009/0068110 A1 | 3/2009 | Shang et al. | |
| 2010/0062978 A1 | 3/2010 | Gotoh et al. | |
| 2011/0039832 A1 | 2/2011 | Van Rijn et al. | |
| 2012/0005767 A1 | 1/2012 | Cohen et al. | |
| 2013/0289020 A1 | 10/2013 | Savory et al. | |
| 2014/0044720 A1 | 2/2014 | Dimitrov et al. | |
| 2014/0045832 A1 | 2/2014 | Balachandran et al. | |
| 2014/0286936 A1 | 9/2014 | Chambers et al. | |
| 2017/0226106 A1 | 8/2017 | Savory et al. | |

FOREIGN PATENT DOCUMENTS

| | | |
|---|---|---|
| AU | 2006-230674 | 11/2006 |
| JP | 2004-203871 | 7/2004 |
| WO | 97/36893 A1 | 10/1997 |
| WO | 01/02392 A1 | 1/2001 |
| WO | 02/08221 A2 | 1/2002 |
| WO | 02/094799 A2 | 11/2002 |
| WO | 02/094799 A3 | 11/2002 |
| WO | 03/076400 A1 | 9/2003 |
| WO | 2004/009587 A1 | 1/2004 |
| WO | 2005/074535 A2 | 8/2005 |
| WO | 2007/115231 A2 | 10/2007 |

(Continued)

OTHER PUBLICATIONS

International Search Report dated Mar. 30, 2020, corresponding to International Application No. PCT/US2019/065600 filed Dec. 14, 2019; 16 pages.
Konishi, Masayuki et al., "Syntheses and Antitrichomonal Activity of 1-(5-Nitro-2-thiazolyl)homopiperazine Deivatives," UDC (1973; Rec'd Aug. 24, 1972) 93(5):684-687.
U.S. Appl. No. 10/287,292, filed May 14, 2019, Fan et al..
Extended European Search Report corresponding to EP Application No. 09825370 dated May 31, 2012; 4 pages.
International Search Report dated Jan. 27, 2010, corresponding to International Application No. PCT/US09/63298 filed Nov. 4, 2009; 7 pages.
International Search Report and Written Opinion dated Apr. 4, 2014 corresponding to PCT Application No. PCT/US2013/072067; 12 pages.
Extended European Search Report corresponding to EP Application No. 13859147.4 dated May 17, 2016; 7 pages.

(Continued)

*Primary Examiner* — Sun Jae Yoo
(74) *Attorney, Agent, or Firm* — Mintz Levin Cohn Ferris Glovsky and Popeo PC

(57) ABSTRACT

Provided herein are methods of treating cancer in an individual in need thereof, the methods comprising administering to the individual a CXCR7 inhibitor. In some embodiments, additional therapeutic agents are used. Also provided herein are methods of preventing precancerous cells expressing FRS2β from developing into cancer, the method comprising administering to an individual having precancerous cells expressing FRS2β a CXCR7 inhibitor. In some embodiments, additional therapeutic agents are used.

20 Claims, 29 Drawing Sheets

(56) References Cited

FOREIGN PATENT DOCUMENTS

| WO | 2007/115231 | A3 | 10/2007 |
|---|---|---|---|
| WO | 2007/115232 | A2 | 10/2007 |
| WO | 2007/115232 | A3 | 10/2007 |
| WO | 2007/126935 | A2 | 11/2007 |
| WO | 2008/008518 | A1 | 1/2008 |
| WO | 2008/011611 | A2 | 1/2008 |
| WO | 2008/011611 | A3 | 1/2008 |
| WO | 2008/020229 | A2 | 2/2008 |
| WO | 2008/020229 | A3 | 2/2008 |
| WO | 2008/069997 | A1 | 6/2008 |
| WO | 2008/073825 | A1 | 6/2008 |
| WO | 2008/112156 | A1 | 9/2008 |
| WO | 2010/054006 | A1 | 5/2010 |
| WO | 2010/069684 | A1 | 6/2010 |
| WO | 2012/022265 | A1 | 2/2012 |
| WO | 2014/085490 | A1 | 6/2014 |

OTHER PUBLICATIONS

Brunn, Anna M. D. et al., "Differential Effects of CXCR4-CXCL12- and CXCR7-CXCL 12-mediated Immune Reactions on Murine $PO_{106-125}$-induced Experimental Autoimmune Neuritis," *British Neuropathological Society* © 2013 (Accepted Article 2013), 40 pages.

Cruz-Orengo, Lillian et al., "CXCR7 antagonism prevents axonal injury during experimental autoimmune encephalomyelitis as revealed by in vivo axial diffusivity," *Journal of Neuroinflammation* (Dec. 6, 2011) 8:170, 39 pages.

Ding, Bi-Sen et al., "Divergent angiocrine signals from vascular niche balance liver regeneration and fibrosis," *Nature* (Nov. 20, 2013) 7 pages.

Konishi, Masayuki et al., Res. Lab. Eisai Co., Ltd. , Tokyo, Japan, *Yakugaku Zasshi*, (1973), 93(5):684-7 CODEN: YKKZAJ; ISSN: 0031-6903 (abstract).

Li, Xiaofeng et al., Activation of CXCR7 Limits Atherosclerosis and Improves Hyperlipedemia by Increasing Cholesterol Uptake in Adipose Tissue, *Circulation* (2014; published online Dec. 27, 2013) 129:1244-1253.

Miao, Zhenhua et al., "CXCR7 (RDC1) promotes breast and lung tumor growth in vivo and is expressed on tumor-associated vasculature," *PNAS* (Oct. 2, 2007) 104(40):15735-15740.

Sartina, Ecaterina et al., "Antagonism of CXCR7 Attenuates Chronic Hypoxia-Induced Pulmonary Hypertension," *Pediatric Research* (Jun. 2012; advance online publication Mar. 28, 2011) 71(6):682-688.

Walters, M. J. et al., "Inhibition of CXCR7 extends survival following irradiation of brain tumours in mice and rats," *British Journal of Cancer* (Jan. 14, 2014) 110:1179-1188.

Wang, Jianhua et al., "The Role of CXCR7/RDC1 as a Chemokine Receptor for CXCL12/SDF-1 in Prostate Cancer," *Journal of Biological Chemistry* (Feb. 15, 2008) 283(7):4283-4294.

Watanabe, Kaori et al., "Pathogenic Role of CXCR7 in Rheumatoid Arthritis," *Arthritis & Rheumatism* (Nov. 30, 2010) 62(11):3211-3220.

Zabel, Brian A. et al., "Elucidation of CXCR7-Mediated Signaling Events and Inhibition of CXCR4-Mediated Tumor Cell Transendothelial Migratoin by CXCR7 Ligands," *The Journal of Immunology* (Jul. 29, 2009) on-line version, 183:0000-0000; 8 pages.

* cited by examiner

|  | $10^4$ cells | $10^3$ cells | $10^2$ cells |
|---|---|---|---|
| Frs2β (+/+) | 4/4 | 4/4 | 0/4 |
| Frs2β (-/-) | 0/4 | 0/4 | 0/4 |

CXCR7 INHIBITORS FOR THE TREATMENT OF CANCER

CROSS-REFERENCES TO RELATED APPLICATIONS

This is an application claiming priority benefit under 35 U.S.C. § 119(e) of U.S. Provisional Application No. 62/778,605 filed Dec. 12, 2018, which is herein incorporated by reference in its entirety for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Tumor tissues are composed of many heterogenous cell types; not only tumor cells but also other cell types including cancer-associated fibroblasts (CAFs), which are a major component of tumor stroma. Recently, much focus has been placed on the tumor microenvironment as a novel therapeutic target, since all these cells appear to support the survival and growth of tumor cells. Accumulating evidence indicates that the tumor cells themselves are heterogenous, including a small number of cancer stem-like cells (CSCs) which are cancer cells with stemness traits, and a large number of rapidly growing differentiated tumor cells. CSCs are thought to control the CSC niche, which is the microenvironment surrounding the CSCs, for their own survival and growth. Inflammatory cytokine-rich environment is thought to be involved in the CSC and tumor microenvironment. Several reports showed that the nuclear factor-κB (NFκB) transcription factor plays key roles in the production of cytokines, including the insulin-like growth factor (IGF) family cytokines and CXC chemokine ligand (CXCL) 12. The IGF family cytokines maintain the undifferentiated state of CSCs and CXCL12 is known to be involved in the chemotaxis of CAFs and CXCL12 itself activates NFκB. NFκB is known to be an inflammatory master transcription factor and is a heterodimeric complex (RelA and p50 or RelB and p52) that binds to IκB in an inactive states. Ligand stimulation leads to phosphorylation of IKKα/β and IκB. Then, the phosphorylated IκB undergoes ubiquitylation/degradation and the released NF-κB heterodimer is transported to the nucleus for transcriptional activation. However, it remains unclear how this occurs at the beginning of tumor development, when there are only a few tumor cells in the apparently normal tissue.

Breast cancer is the most common cancer among women. Recently much attention has been paid for prevention of cancer in order to reduce the number of patients. Emerging evidence suggests that inflammation contributes to occurrence of breast cancer, however, underlying molecular mechanisms remain unknown. Despite of the advancements in therapeutic strategies, the disease-related mortality is still high because of frequently occurring recurrence. Accumulating evidence suggests that CSCs are the major cause of the poor prognosis. They are resistant to a variety of stressful conditions and thought to be responsible for tumor initiation, recurrence and therapeutic resistance. Breast cancer tissues contain ample amount of stroma in many cases, indicating that the CAF-containing tumor microenvironment plays important roles in breast cancer. Thus, there is a great hope to target the tumor microenvironment or CSC niche for eliminating CSCs, as an effective therapeutic strategy for breast cancer. Despite this goal, reliably effective treatments are still needed.

A part of breast cancer belong to the human epidermal growth factor receptor 2 (HER2)/ErbB2 positive subtype, in which HER2 gene amplification or/and HER2 protein overexpression are observed in the cancer cells. Herceptin, a humanized antibody against HER2, is effective against HER2-positive cases; however, herceptin-resistance or recurrence still raises serious problems. Mouse mammary tumor virus (MMTV)-ErbB2 transgenic mice have ErbB2 overexpression in the mammary tissues, which causes tumorigenesis. Mammary tissues are comprised of many branching tubules that terminate in alveoli, and both of them expand in pregnancy. The epithelium is comprised of two major cell layers: the luminal cells that surround the inner lumen and the highly elongated myoepithelial on the other side. Luminal progenitor cells are thought to exist in the luminal cell layer. Evidence suggests that the luminal progenitor cells are cells of origin of mammary tumorigenesis in this model, and in human breast cancer. However, effective treatments to prevent or treat tumorigenesis of these cells remain active areas of study.

ErbB2 homodimerizes or heterodimerizes with other ErbB family members and activates the extracellular-signal regulated protein kinase (ERK) and phosphoinositide 3-kinase (PI3K) signaling pathways, leading to many aspects of tumor biology. The ErbB-ERK signaling increases cell proliferation and differentiation, depending on the cellular context. The ErbB-PI3K signaling activates NFκB.

An adaptor protein FRS2β, also called as SNT-2 or FRS3, is expressed abundantly in the brain, but only in a few areas in other tissues, whereas another FRS2 family member FRS2α is expressed abundantly in most tissues. Further information on FRS2β expression is discussed in Gotoh et al. FEBS Lett. 2004. 564(1-2):14-8. FRS2β, but not FRS2α, constitutively binds to the ErbB family members including ErbB2, which binds to activated ERK for feedback inhibition and fine-tunes the ErbB-ERK signaling. FRS2β also induces ubiquitylation and degradation of ErbB1/2. However, the in vivo role of FRS2β, especially in tumor development, remains unknown.

Collectively, there remains a need in the art to identify processes that lead to the development of CSC niche environments and agents that can target appropriate agents to modulate, reduce, or prevent tumor development. The present invention addresses this need and provides related advantages as well.

BRIEF SUMMARY OF THE INVENTION

In one aspect, provided herein are methods of treating cancer in an individual in need thereof, said method comprising administering to the individual a CXCR7 inhibitor, wherein the individual has aberrant expression of FRS2β.

In another aspect provided herein are methods of preventing precancerous cells expressing FRS2β from developing into cancer, said method comprising administering to an individual having precancerous cells expressing FRS2β a CXCR7 inhibitor.

In some embodiments, the CXCR7 inhibitor has the structure of Formula I and/or II:

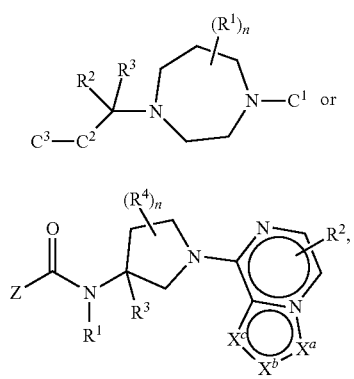

the definitions for each variable group are further detailed below.

In some embodiments, the inhibitor of CXCR7 has the structure of Compound 1

(Compound 1)

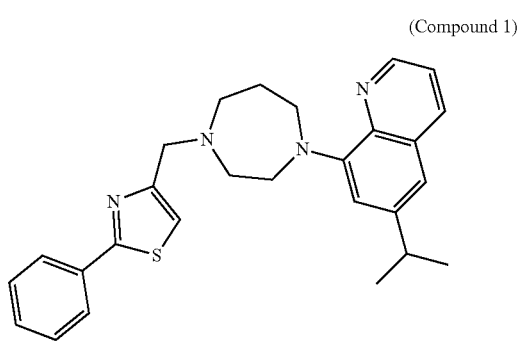 [SMILES: CC(C)c1cc(N2CCCN(Cc3csc(-c4ccccc4)n3)CC2)c2ncccc2c1]

or a pharmaceutically acceptable salt thereof.

In some embodiments, the inhibitor of CXCR7 has the structure of Compound 2

(Compound 2)

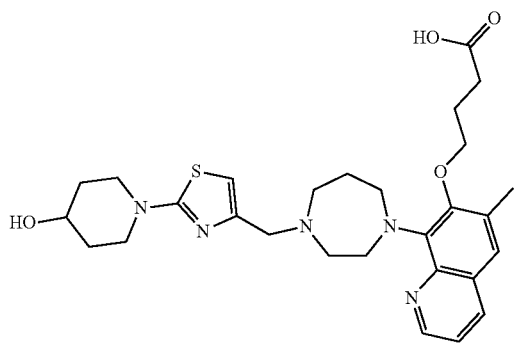

or a pharmaceutically acceptable salt thereof.

In some embodiments, the inhibitor of CXCR7 has the structure of Compound 3

(Compound 3)

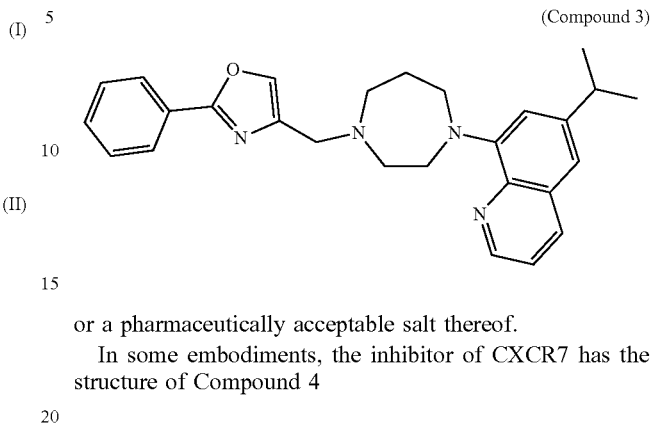

or a pharmaceutically acceptable salt thereof.

In some embodiments, the inhibitor of CXCR7 has the structure of Compound 4

(Compound 4)

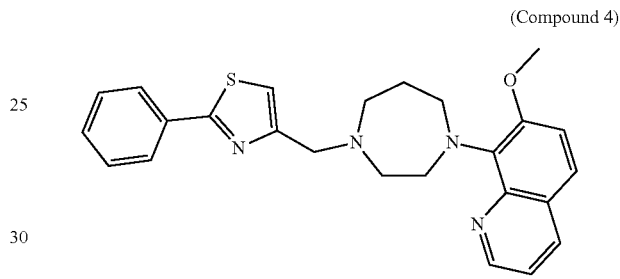

or a pharmaceutically acceptable salt thereof.

In some embodiments, the inhibitor of CXCR7 has the structure of Compound 5

(Compound 5)

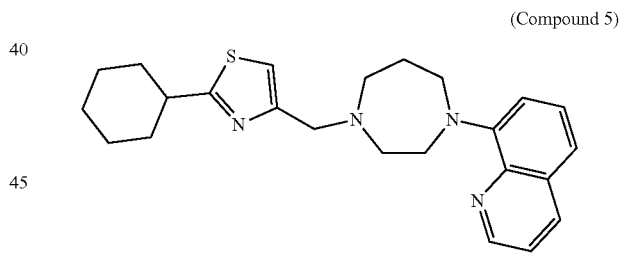

or a pharmaceutically acceptable salt thereof.

In some embodiments, the inhibitor of CXCR7 has the structure of Compound 6

(Compound 6)

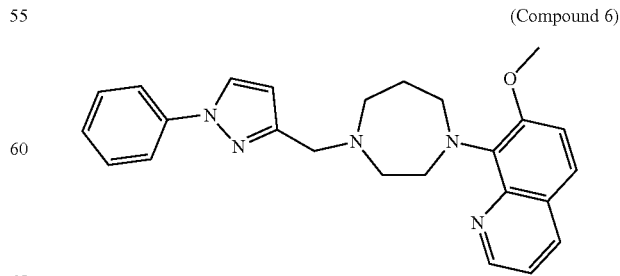

or a pharmaceutically acceptable salt thereof.

In some embodiments, the CXCR7 inhibitor has the structure of Compound 7

(Compound 7)

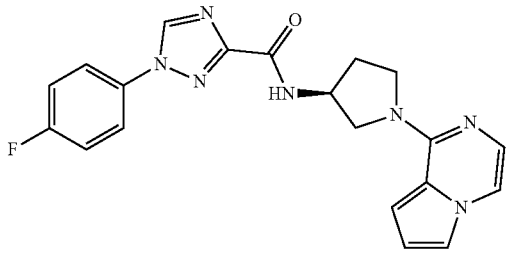

or a pharmaceutically acceptable salt thereof.

In some embodiments, the inhibitor of CXCR7 has the structure of Compound 8

(Compound 8)

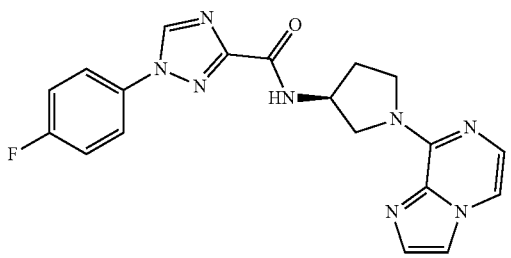

or a pharmaceutically acceptable salt thereof.

In some embodiments, the inhibitor of CXCR7 has the structure of Compound 9

(Compound 9)

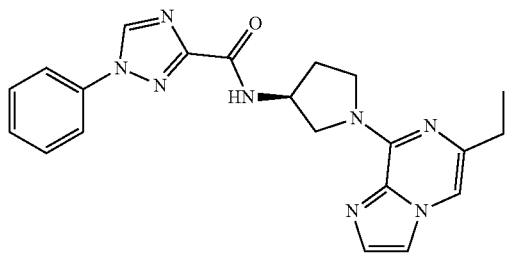

or a pharmaceutically acceptable salt thereof.

In some embodiments, the methods provided herein use one or more therapeutic agents. In some embodiments, the one or more therapeutic agents are an IGF1 inhibitor and/or a CXCR4 inhibitor. In some embodiments, the IGF1 inhibitor is an anti-IGF1 antibody.

Other objects, features, and advantages of the present invention will be apparent to one of skill in the art from the following detailed description and figures.

Figure 1A:
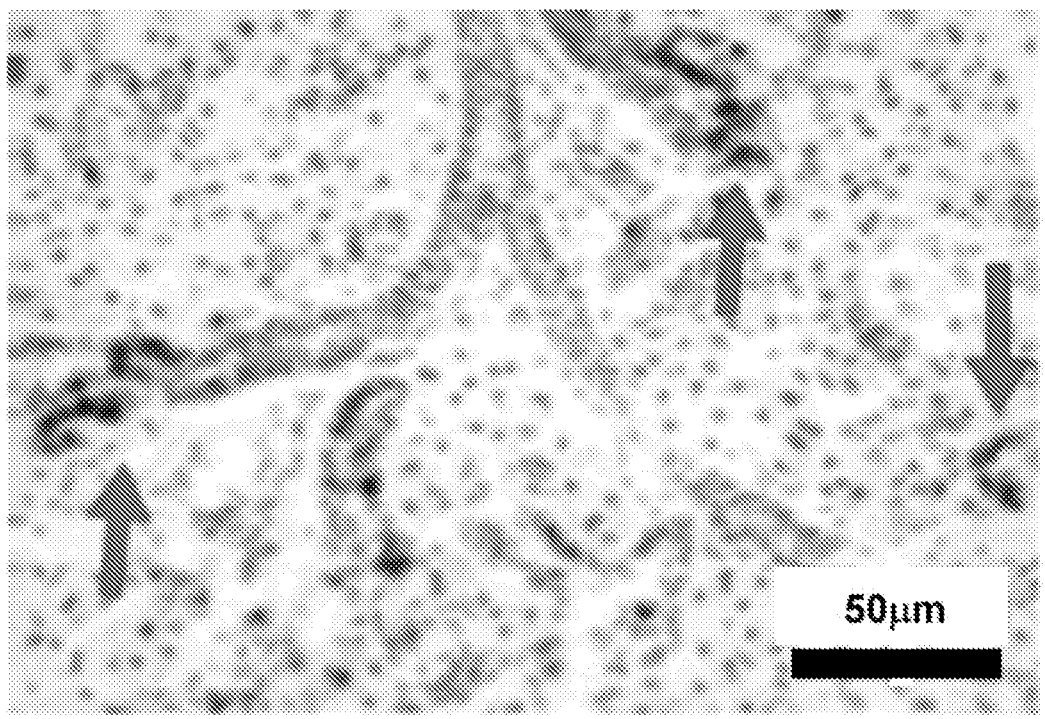
FIG. 1A-H Deficiency of FRS2β expressed in luminal cells greatly delays mammary tumorigenesis (A) Representative images of β-galactosidase staining for mature female mammary glands of heterozygote of the Frs2β mutant allele. Red arrows indicate FRS2β positive cells. (B) Schematic of the mammary glands. Many branching tubles are surrounded by an inner layer of luminal epithelial cells and an outer layer of myoepithelial epithelial cells. (C) Immunohistological staining for female mammary glands by anti-FRS2β antibody and phospho-histone H3 antibody (upper panel) or DAPI (lower panel). (D) Immunohistological staining for female mammary glands by anti-FRS2β antibody and Cytokeratin 18 (upper panels) or Cytokeratin 14 (lower panels). (E) Representative NMR imaging of the mammary tumors shown in the frontal planes of the mice at 14 weeks after observation started. Left side is head and right side is abdomen. (F) Tumor growth in MMTV-neu (+)/Frs2β (+/+) and MMTV-neu (+)/Frs2β (−/−) mice. Tumor sizes were measured once a week for 14 weeks (mean±SEM, n=15). Expression level of FRS2β was compared by qRT-PCR analysis among virgin, pregnant and lactate (mean±SEM, n=4, **p<0.005, *p<0.01). (G) Representative Hematoxylin and eosin (HE) stained sections of mammary tumors. (H) Immunohistochemical staining for Frs2β (+/+) and Frs2β (−/−) mammary tumors using antibodies against αSMA. Scale bar: 100 μm.
Figure 1B:
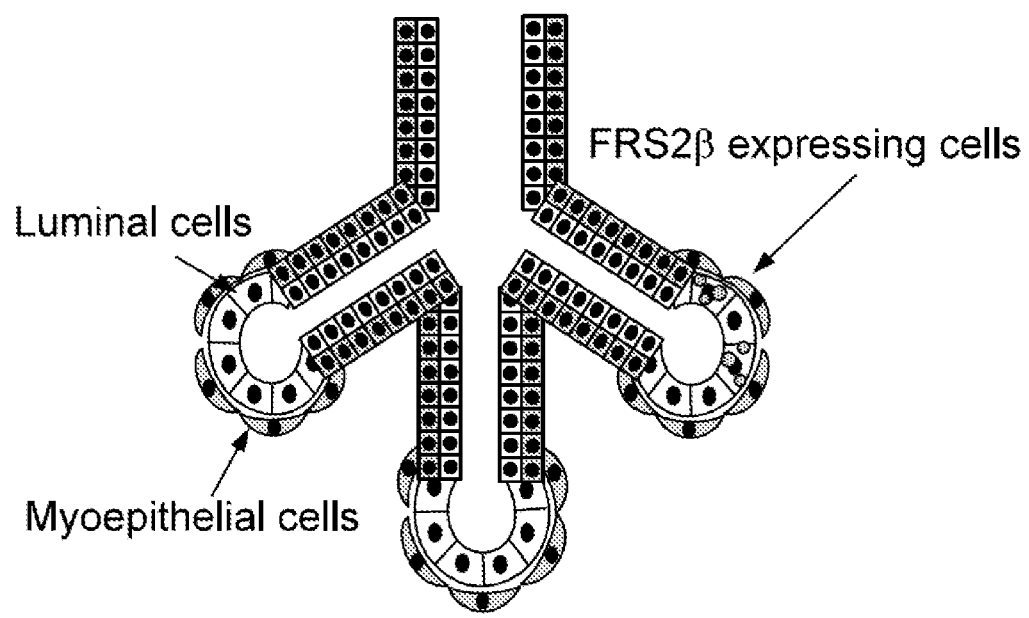

precancerous mammary epithelial cells in the upper chamber. (B) Representative images of tumor sphere formation in the presence of Frs2β (+/+) mammary epithelial cells treated with control IgG (400 nM) or IGF1 neutralizing antibody (Nab) (400 nM). N.T., not treated (without co-culture with mammary epithelial cells). Scale bar: 100 ∝μ. (C) Quantification of tumor sphere-forming efficiency. Results are shown as means±SEM. n=4. *p<0.001, p<0.01. (D) Schematic of co-culture of Frs2β (+/+) or Frs2β (−/−) mammary cells in the lower chamber with Frs2β (+/+) or Frs2β (−/−) CAFs in the upper chamber. (E) Expression levels of Cxcl12 was compared between Frs2β (+/+) or Frs2β (−/−) mammary cells on the upper chamber by qPCR. Results were shown as mean±SEM. n=6. * * *p<0.001. (F) Representative images of migrated Frs2β (+/+) CAFs co-cultured with Frs2β (+/+) or Frs2β (−/−) mammary cells in the upper chamber for 24 hours. (G) Quantification of migrated Frs2β (+/+) CAFs. Results were shown as mean±SEM. n=4. p<0.01. (H) Representative images of migrated CAFs co-cultured with Frs2β (+/+) cancer cells for 24 hr. Cells were treated with indicated concentration of Compound 1 and/or+0.1 mg/mL AMD3100) or control. (I) Quantification of the migrated CAFs co-cultured with Frs2β (+/+) cancer cells for 24 hr. Results were shown as mean±SEM. n=4. *p<0.001 and **p<0.01.

FIG. 5A-K FRS2β-dependent increase in activation of AKT-NFκB increases the production of IGF1 and CXCL12, promoting tumorigenesis. (A) Schematic of DHMEQ treatment of cultured Frs2β (+/+) precancerous mammary epithelial cells in vitro. (B) Expression levels of Igf1, Cxcl12, and IκBα in Frs2β (+/+) precancerous mammary epithelial cells treated with the indicated concentration of DHMEQ were compared by qPCR. Results are shown as means±SEM. n=4. p<0.01. (C) Immunoblotting analysis of the indicated proteins in the lysate of Frs2β (+/+) or Frs2β (−/−) precancerous mammary tissues. Actin was used as a loading control. (D) Immunoblotting analysis of cytoplasmic and nuclear expression levels of the indicated proteins (control as a nuclear protein) in the lysate of Frs2β (+/+) or Frs2β (−/−) mammary tissues. PARP1 was used as a representative protein in nucleus. Actin was used as a loading control. (E) Immunoblotting analysis of the indicated proteins in the lysate of Frs2β (+/+) or Frs2β (−/−) mammary tissues. Actin was used as a loading control. (F) Schematic of DHMEQ treatment of Frs2β (+/+) mice in vivo. The mice were intraperitoneally injected with 10 μg/g DHMEQ once a day for 3 weeks. (G) Immunohistochemical staining for Frs2β (+/+) mammary tissues with or without 3-week treatment with 10 μg/g DHMEQ, or Frs2β (−/−) mammary tissues, using antibodies against RelA. Scale bar: 50 ∝μ. (H) Expression levels of Igf1 and Cxcl12 in Frs2β (+/+) mammary tissues, with or without 3-week treatment with 10 μg/g DHMEQ. N.T., not treated. Results are shown as means±SEM. n=4. *p<0.001 and **p<0.01 (I) Treatment of mice with a CXCR7 inhibitor and/or an IGF1 antibody reduces tumor volume. Frs2β (+/+) tumor sphere cells were inoculated into mammary fat pads of 8-week-old virgin female MMTV-neu (+)/Frs2β (+/+) mice. After 7 days, the mice were intraperitoneally injected with 0.1 μg/g IGF1 antibody (R&D Biosystems) once per week and/or 1 μg/g of AMD3100 (Sigma) one a day and 1.5 μg/g of Compound 1 once a day. Representative tumors were photographed on day 35 after transplantation CXCL12 Inh, combination of AMD3100 and CCX771. Tumor volumes (J) and weights (K) were measured in mice treated as in (I). Results were shown as mean±SEM, n K=4, *p<0.05.

FIG. 6 A-G FRS2β-expressing tumor cells produce IGF1 and CXCL12 and are associated with abundant stroma and poor prognosis (A) Immunohistochemical staining for Frs2β (+/+) mammary tumors by anti-FRS2b and anti-ErbB2 antibodies. Scale bar, 25 ∝μ. (B) Expression levels of Cxcl12 and Igf1 were compared between Frs2β (+/+) and Frs2β (−/−) tumor cells by qPCR. Results are shown as means±SEM. n=4. ***p<0.001. (C) Immunohistochemical staining with anti-IGF1 and anti-CXCL12 antibodies. Scale bar, 200 ∝μ. (D) Tissue arrays were subjected to immunohistochemical staining with anti-FRS2b antibody or Masson's trichrome staining to detect collagen in stroma. Arrows indicate the stroma area. Scale bar: 50 ∝μ. (E) Tumor samples were classified into three groups according to the ratio of the tumor stroma area to the total tumor area (+: 0-10%, ++; 10-20%, +++; >20%). Median of FRS2b staining levels was used for cut-off values. n=30. (F) Kaplan-Meier survival curve, generated using the Uppsala cohort (GSE3494). Medians were used for cut-off value. P-value was obtained by log-rank test. (G) FRS2b may trigger cytokine production in a subset of luminal cells, leading to creation of a cytokine-rich precancerous microenvironment (upper left panel). Once CSCs appear in the precancerous microenvironment, they may be able to self-renew in the presence of IGF1 and produce tumor cells with the help of CXCL12-mobilized stromal cells, which subsequently become CAFs. CSCs and tumor cells may produce IGF1 and CXCL12 on their own, leading to rapid growth and tumorigenesis (lower left panel). Without FRS2β, cytokines remain at low levels, and no appropriate precancerous microenvironment is created (upper right panel); even when CSCs appear, they cannot efficiently grow (lower right panel).

DETAILED DESCRIPTION OF THE INVENTION

I. General

The current disclosure demonstrates that aberrant FRS2β expression maintains a suitable microenvironment condition for tumor growth and plays critical roles in creating the cytokine-rich CSC niche. Surprisingly, the deleterious effects of this expression can be effectively modulated by administering a CXCR7 inhibitor or a CXCR7 inhibitor in combination with another therapeutic agent.

II. Definitions

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "cycloalkenyl" refers to a cycloalkyl group having at least one double bond between ring vertices. Examples of cycloalkenyl are cyclopentenyl and cyclohexenyl. The term "spirocycloalkyl" refers to a cycloalkyl group in which a single ring vertex is attached to two other non-hydrogen portions of the molecule. A spirocycloalkyl substituent is one in which two carbon atoms of an alkylene chain (typically the termini of the alkylene chain) are attached to the same carbon atom in the remainder of the molecule. The term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycylic ring system. Non limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkyl group can be attached to the remainder of the molecule through a ring carbon or a heteroatom.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

As used herein, a wavy line, "〜", that intersects a single, double or triple bond in any chemical structure depicted herein, represent the point attachment of the single, double, or triple bond to the remainder of the molecule.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

The term "arylalkyl" is meant to include those radicals in which an aryl group is attached to an alkyl group (e.g., benzyl, phenethyl, and the like). Similarly, the term "heteroaryl-alkyl" is meant to include those radicals in which a heteroaryl group is attached to an alkyl group (e.g., pyridylmethyl, thiazolylethyl, and the like).

The above terms (e.g., "alkyl," "aryl" and "heteroaryl"), in some embodiments, will include both substituted and unsubstituted forms of the indicated radical. Preferred substituents for each type of radical are provided below.

Substituents for the alkyl radicals (including those groups often referred to as alkylene, alkenyl, alkynyl and cycloalkyl) can be a variety of groups selected from: -halogen, —OR', —NR'R", —SR', —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NH—C($NH_2$)=NH, —NR'C($NH_2$)=NH, —NH—C($NH_2$)=NR', —S(O)R', —S(O)$_2$R', —S(O)$_2$NR'R", —NR'S(O)$_2$R", —CN and —$NO_2$ in a number ranging from zero to (2 m'+1), where m' is the total number of carbon atoms in such radical. R', R" and R'" each independently refer to hydrogen, unsubstituted $C_{1-8}$ alkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, substituents for the aryl and heteroaryl groups are varied and are generally selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R'", —NH—C($NH_2$)=NH, —NR'C($NH_2$)=NH, —NH—C($NH_2$)=NR', —S(O)R', —S(O)$_2$R', —S(O)$_2$NR'R", —NR'S(O)$_2$R", —$N_3$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—($CH_2$)$_q$—U—, wherein T and U are independently —NH—, —O—, —$CH_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR" or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

As used herein, the term "heteroatom" is meant to include oxygen (O), nitrogen (N), sulfur (S) and silicon (Si).

As used herein, the term "progenitor cells" and "stem cells" are used interchangeably. "Progenitor cells" and "stem cells" refer to cells that, in response to certain stimuli, can form differentiated cell lineages, including but not limited to hematopoietic, mesenchymal, epithelial, neuronal, renal or myeloid cells. The presence of progenitor/stem cells can be assessed by the ability of the cells in a sample to form colony-forming units of various types, including, for example, CFU-GM (colony-forming units, granulocyte-macrophage); CFU-GEMM (colony-forming units, multipotential); BFU-E (burst-forming units, erythroid); HPP-CFC (high proliferative potential colony-forming cells); or other types of differentiated colonies which can be obtained in culture using known protocols. Hematopoetic progenitor/stem cells are often positive for CD34. Some stem cells do not contain this marker, however. These CD34+ cells can be assayed using fluorescence activated cell sorting (FACS) and thus their presence can be assessed in a sample using this technique. Alternatively, such cells can be assayed by FACS for the presence of c-kit receptor (CD117), absence of lineage specific markers (e.g., CD2, CD3, CD4, CD5, CD8, NK1.1, B220, TER-119, and Gr-1 in mice and CD3, CD14, CD16, CD19, CD20 and CD56 in humans).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. In some embodiments, the compounds of the invention are present in an enantiomerically enriched form, wherein the amount of enantiomeric excess for a particular enantiomer is calculated by known methods. The preparation of enantiomerically enriched forms is also well known in the art and can be accomplished using, for example, chiral resolution via chromatography or via chiral salt formation. Additionally, different conformers are contemplated by the present invention, as well as distinct rotamers. Conformers are conformational isomers that can differ by rotations about one or more σ bonds. Rotamers are conformers that differ by rotation about only a single σ bond. Still further, the compounds of the present invention may also contain unnatural proportions of atomic isotopes at one or more of the atoms that constitute such compounds. Accordingly, in some embodiments, the compounds of the invention are present in isotopically enriched form. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere with this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

"CXCR7" also referred to as "RDC1" or "CCXCKR2" refers to a seven-transmembrane domain presumed G-protein coupled receptor (GPCR). The CXCR7 dog ortholog was originally identified in 1991. See, Libert et al. *Science* 244:569-572 (1989). The dog sequence is described in Libert et al., *Nuc. Acids Res.* 18(7):1917 (1990). The mouse sequence is described in, e.g., Heesen et al., *Immunogenetics* 47:364-370 (1998). The human sequence is described in, e.g., Sreedharan et al., *Proc. Natl. Acad. Sci.* USA 88:4986-4990 (1991), which mistakenly described the protein as a receptor of vasoactive intestinal peptide.

The term "therapeutically effective amount" means the amount of the subject compound that will elicit the biological or medical response of a cell, tissue, system, or animal, such as a human, that is being sought by the researcher, veterinarian, medical doctor or other treatment provider.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

III. Detailed Description of Embodiments

A. Methods

In one aspect, provided herein are methods of treating cancer in an individual in need thereof, said method comprising administering to the individual a CXCR7 inhibitor, wherein the individual has aberrant expression of FRS2β.

In another aspect provided herein are methods of preventing precancerous cells expressing FRS2β from developing into cancer, said method comprising administering to an individual having precancerous cells expressing FRS2β a CXCR7 inhibitor.

As described in the background section, FRS2β is expressed abundantly in the brain, but only in a few areas in other tissues. Thus, many tissues do not naturally express FRS2β. As shown herein, aberrant expression of FRS2β in cells that otherwise do not express this protein can provide a CSC niche and lead to tumorgenesis.

It is understood that aberrant expression refers to expression of a protein in a cell, tissue, organ or body fluid of a patient that does not normally produce the protein in a healthy individual (inappropriate expression) or expression of higher levels of a protein in a cell, tissue, organ or body fluid of a subject than are detected in the same type of cell, tissue, organ or body fluid of a healthy individual (differential expression). In some embodiments aberrant expression of FRS2β is at least about 3%, at least about 5%, least about 10%, at least about 15%, at least about 20%, at least about 25%, at least about 30%, at least about 35%, at least about 40%, at least about 45%, at least about 50% or greater FRS2β expression than in a healthy individual. It will be understood by the skilled artisan that FRS2β expression can determined using known methods in the art. In some embodiments, FRS2β expression can be detected as described in the disclosed methods. In some embodiments, FRS2β expression can be detected using immunohistochemistry. In various embodiments, aberrant expression is detected in an ELISA assay.

There are many CXCR7 inhibitors known in the art, and further details of possible CXCR7 inhibitors useful in the present disclosure are further discussed in the sections below.

A preferred method of treating cancer, includes administering a therapeutically effective amount of one or more of the previously mentioned compounds (or salts thereof) to a cancer patient for a time sufficient to treat the cancer.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

In some cases, CXCR7 inhibitors are administered to treat cancer, e.g., carcinomas, gliomas, mesotheliomas, melanomas, lymphomas, leukemias (including acute lymphocytic leukemias), adenocarcinomas, breast cancer, ovarian cancer, cervical cancer, glioblastoma, leukemia, lymphoma, prostate cancer, and Burkitt's lymphoma, colon cancer, colorectal cancer, cancer of the esophagus, stomach cancer, pancreatic cancer, hepatobiliary cancer, cancer of the gallbladder, cancer of the small intestine, rectal cancer, kidney cancer, renal cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma (see, CANCER: PRINCIPLES AND PRACTICE (DeVita, V. T. et al. eds 1997) for additional cancers).

In some embodiments, the cancer treated herein is breast cancer.

In some embodiments, the individual has been diagnosed with having aberrant expression of FRS2β prior to administration of a CXCR7 inhibitor or an additional therapeutic agent.

B. Inhibitors of CXCR7

In some embodiments, inhibitors of CXCR7 has the structure of Formula I

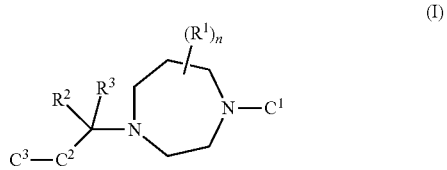

or pharmaceutically acceptable salts, hydrates, N-oxides, isotopically enriched or enantiomerically enriched versions thereof, wherein the subscript n is an integer of from 0 to 2;

each R', when present, is independently selected from the group consisting of $C_{1-4}$ alkyl, $-CO_2R^a$, $-X-CO_2R^a$, $-CONR^aR^b$ and $-X-CONR^aR^b$;

$R^2$ and $R^3$ are each members independently selected from the group consisting of H, $-R^a$, $-XR^a$, $-XNR^aR^b$, $-XNHCONR^aR^b$, $-XNHCOR^a$, $-X-O-CONR^aR^b$, $-XNHSO_2R^a$, $-CO_2R^a$, $-X-CO_2R^a$, $-CONR^aR^b$ and $-X-CONR^aR^b$; or taken together are oxo;

$C^1$ is selected from the group consisting of monocyclic or fused-bicyclic aryl and heteroaryl, wherein the heteroaryl group has from 1-3 heteroatoms as ring members selected from N, O and S; and wherein said aryl and heteroaryl groups are optionally substituted with from 1 to 3 $R^4$ substituents;

$C^2$ is monocyclic four-, five-, six- or seven-membered ring selected from the group consisting of benzene, heteroaromatic, cycloalkane, and heterocycloalkane, wherein the heteroaromatic and heterocycloalkane rings have from 1-3 heteroatoms as ring members selected from N, O and S; and wherein each of said monocyclic $C^2$ rings are optionally substituted with from 1 to 3 $R^5$ substituents;

$C^3$ is selected from the group consisting of hydrogen, $C_{1-8}$ alkyl, $C_{3-8}$ cycloalkyl, aryl, aryl-$C_{1-4}$ alkyl, heteroaryl, heteroaryl-$C_{1-4}$ alkyl, and four- to six-membered heterocycloalkyl, wherein the heterocycloalkyl group or portion has from 1-3 heteroatoms selected from N, O and S, and wherein the heteroaryl group has from 1-3 heteroatoms as ring members selected from N, O and S, and each $C^3$ is optionally substituted with from 1-3 $R^6$ substituents;

each $R^4$ is independently selected from the group consisting of halogen, $-CN$, $-NO_2$, $-R^c$, $-CO_2R^a$, $-NR^aR^b$, $-OR^a$, $-X-CO_2R^a$, $-CONR^aR^b$ and $-X-CONR^aR^b$;

wherein within each of $R^1$, $R^2$, $R^3$ and $R^4$, each $R^a$ and $R^b$ is independently selected from hydrogen, $C_{1-8}$ alkyl, $C_{3-7}$ cycloalkyl, $C_{1-8}$ haloalkyl, and four- to six-membered heterocycloalkyl, or when attached to the same nitrogen atom can be combined with the nitrogen atom to form a four-, five- or six-membered ring having from 0 to 2 additional heteroatoms as ring members selected from N, O or S; within $R^4$ each $R^c$ is independently selected from the group consisting of $C_{1-8}$ alkyl, $C_{1-8}$ haloalkyl, $C_{3-6}$ cycloalkyl, aryl and heteroaryl, and wherein the aliphatic and cyclic portions of $R^a$, $R^b$ and $R^c$ are optionally further substituted with from one to three halogen, hydroxy, methyl, alkoxy, amino, alkylamino, dialkylamino, carboxamide, carboxy alkyl ester, carboxylic acid, heteroaryl, and four- to six-membered heterocycloalkyl groups; and wherein the heterocycloalkyl portions of $R^2$, $R^3$ and $R^4$ are optionally substituted with oxo; and optionally when two $R^4$ substituents are on adjacent atoms, are combined to form a fused five or six-membered ring having carbon and oxygen atoms as ring members;

each $R^5$ is independently selected from the group consisting of halogen, $-CN$, $-NO_2$, $-R^f$, $-CO_2R^d$, $-COR^d$, $-NR^dR^e$, $-OR^d$, $-X-CO_2R^d$, $-CONR^dR^e$ and $-X-CONR^dR^e$; wherein each $R^d$ and $R^e$ is independently selected from hydrogen, $C_{1-8}$ alkyl, $C_{1-8}$ haloalkyl, $C_{3-6}$ cycloalkyl, $C_{3-6}$ cycloalkyl-alkyl, and four- to six-membered heterocycloalkyl or when attached to the same nitrogen atom can be combined with the nitrogen atom to form a five or six-membered ring having from 0 to 2 additional heteroatoms as ring members selected from N, O or S; each $R^f$ is independently selected from the group consisting of $C_{1-8}$ alkyl, $C_{1-8}$ haloalkyl, and $C_{3-6}$ cycloalkyl, and wherein the aliphatic and cyclic portions of $R^d$, $R^e$ and $R^f$ are optionally further substituted with from one to three halogen, hydroxy, methyl, alkoxy, amino, alkylamino, dialkylamino, carboxamide, carboxy alkyl ester, carboxylic acid, heteroaryl, four- to six-membered heterocycloalkyl groups;

each $R^6$ is independently selected from the group consisting of halogen, $-CN$, $-NO_2$, $-R^i$, $-CO_2R^g$, $-COR^g$, $-NR^gR^h$, $-OR^g$, $-X-CO_2R^g$, $-X-COR^g$, $-CONR^gR^h$ and $-X-CONR^gR^h$, wherein each $R^g$ and $R^h$ is independently selected from hydrogen, $C_{1-8}$ alkyl and $C_{1-8}$ haloalkyl; each $R^i$ is independently selected from the group consisting of $C_{1-8}$ alkyl and $C_{1-8}$ haloalkyl; and each X is a linking group having the formula $-(CH_2)_mO(CH_2)_p-$, wherein the subscripts m and p are integer of from 0 to 5, and m+p is from 0 to 6, wherein the methylene groups are optionally substituted with one or two methyl groups.

In some embodiments, the inhibitor of CXCR7 has the structure of Compound 1

(Compound 1)

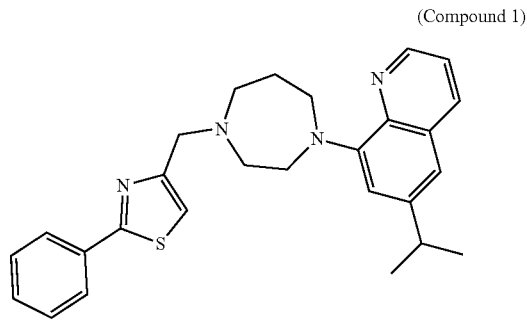 [SMILES: CC(C)c1cc(N2CCCN(Cc3csc(-c4ccccc4)n3)CC2)c2ncccc2c1]

or a pharmaceutically acceptable salt thereof.

In some embodiments, the inhibitor of CXCR7 has the structure of Compound 2

(Compound 2)

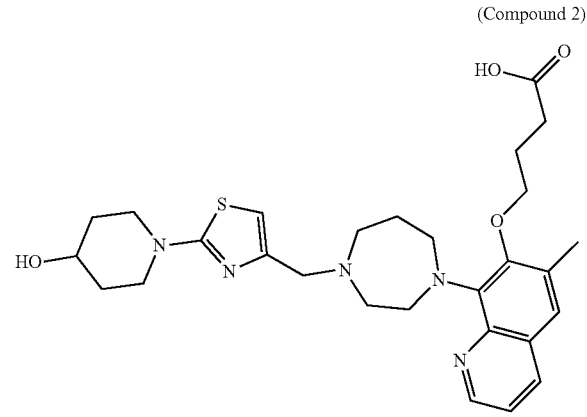 [SMILES: Cc1cc2cccnc2c(N2CCCN(Cc3csc(N4CCC(O)CC4)n3)CC2)c1OCCCC(=O)O]

or a pharmaceutically acceptable salt thereof.

In some embodiments, the inhibitor of CXCR7 has the structure of Compound 3

(Compound 3)

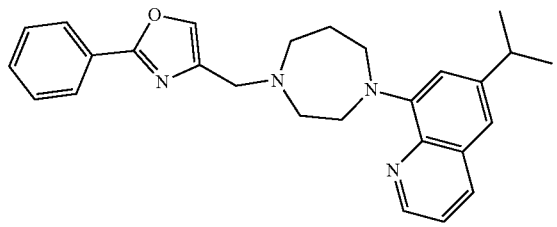

or a pharmaceutically acceptable salt thereof.

In some embodiments, the inhibitor of CXCR7 has the structure of Compound 4

(Compound 4)

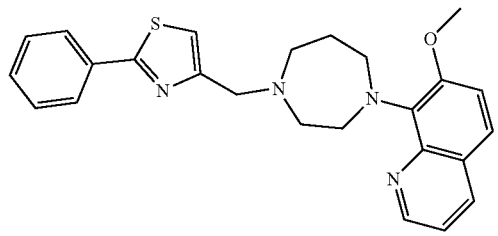

or a pharmaceutically acceptable salt thereof.

In some embodiments, the inhibitor of CXCR7 has the structure of Compound 5

(Compound 5)

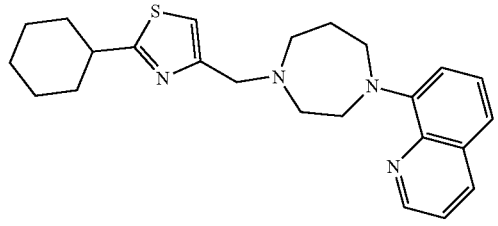

or a pharmaceutically acceptable salt thereof.

In some embodiments, the inhibitor of CXCR7 has the structure of Compound 6

(Compound 6)

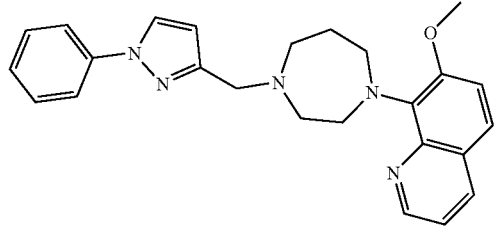

or a pharmaceutically acceptable salt thereof.

In some embodiments, the CXCR7 inhibitor is selected from the compounds or pharmaceutical compositions disclosed in PCT publication No. WO2010/054006 stemming from PCT Application No. US2009/063298, filed Nov. 4, 2009 by ChemoCentryx, the content of which is incorporated herein for all purposes.

In some embodiments, inhibitors of CXCR7 has the structure of Formula II (II)

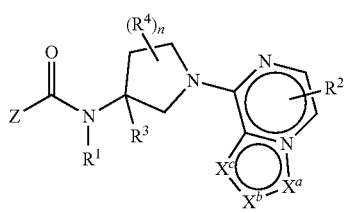

or a pharmaceutically acceptable salt, hydrate, N-oxide, isotopically enriched or enantiomerically enriched version or a rotamer thereof, wherein each of ring vertices $X^a$, $X^b$ and $X^c$ is independently selected from the group consisting of N, NH, N($R^2$), O, CH and C($R^2$);

the subscript n is 0, 1 or 2;

Z is selected from the group consisting of (i) monocyclic or fused-bicyclic aryl and heteroaryl, wherein the heteroaryl group has from 1-4 heteroatoms as ring members selected from N, O and S; and wherein said aryl and heteroaryl groups are optionally substituted with from 1 to 5 $R^5$ substituents;

(ii) monocyclic four-, five-, six- or seven-membered ring selected from the group consisting of cycloalkane, and heterocycloalkane, wherein the heterocycloalkane rings have from 1-3 heteroatoms as ring members selected from N, O and S; and wherein each of said monocyclic Z rings are optionally substituted with from 1 to 3 $R^5$ substituents;

$R^1$ is a member selected from the group consisting of H and $C_{1-8}$ alkyl, wherein the alkyl portion is optionally substituted with halogen, —$NR^aR^b$, —$OR^a$, —$CO_2R^a$, and —$CONR^aR^b$;

each $R^2$ is independently selected from the group consisting of H, halogen, CN, $C_{1-8}$ alkyl, $C_{1-8}$ haloalkyl, $C_{1-8}$ hydroxyalkyl, —$OR^a$, —$CO_2R^a$, —X—$CO_2R^a$, —$NR^aR^b$, —$CONR^aR^b$ and —X—$CONR^aR^b$;

$R^3$ is a member selected from the group consisting of H, $C_{1-8}$ alkyl, $C_{1-8}$ haloalkyl, $C_{1-8}$ hydroxyalkyl, —$CO_2R^a$, —X—$CO_2R^a$, —$CONR^aR^b$ and —X—$CONR^aR^b$;

each $R^4$, when present, is a member independently selected from the group consisting of $C_{1-8}$ alkyl, $C_{1-8}$ haloalkyl, $C_{1-8}$ hydroxyalkyl, —$OR^a$, —$CO_2R^a$, —X—$CO_2R^a$, —$CONR^aR^b$ and —X—$CONR^aR^b$;

each $R^5$ is a member independently selected from the group consisting of halogen, CN, —X—CN, $C_{1-8}$ alkyl, $C_{3-8}$ cycloalkyl, $C_{3-8}$ cycloalkenyl, $C_{3-5}$ spirocycloalkyl, $C_{2-8}$ alkenyl, $C_{2-8}$ alkynyl, $C_{1-8}$ haloalkyl, $C_{1-8}$ hydroxyalkyl, —$OR^a$, —$CO_2R^a$, —X—$CO_2R^a$, —$NR^aR^b$, —$CONR^aR^b$, —X—$CONR^aR^b$, aryl, 5- or 6-membered heteroaryl, and 3-, 4-, 5- or 6-membered heterocyclic wherein the heteroatoms present as ring vertices of the heteroaryl and heterocyclic rings are selected from N, O and S, and wherein the aryl, heteroaryl and heterocyclic portions of $R^5$ are optionally further substituted with 1-3 $R^a$;

each $R^a$ and $R^b$ is independently selected from the group consisting of hydrogen, hydroxyl, halogen, cyano, $C_{1-8}$ alkyl, $C_{1-8}$ alkoxy, $C_{1-8}$ haloalkyl, $C_{3-6}$ cycloalkyl, $C_{3-6}$ cycloalkylalkyl, amino, $C_{1-8}$ alkylamino, di $C_{1-8}$ alkylamino, carboxamide, carboxy $C_{1-4}$ alkyl ester, carboxylic acid, and $—SO_2—C_{1-8}$ alkyl;

each X is a $C_{1-4}$ alkylene linking group or a linking group having the formula $—(CH_2)_mO(CH_2)_p—$, wherein the subscripts m and p are integer of from 0 to 5, and m+p is from 0 to 6, wherein any of the methylene portions of X are optionally substituted with one or two methyl groups.

In some embodiments, the CXCR7 inhibitor has the structure of Compound 7

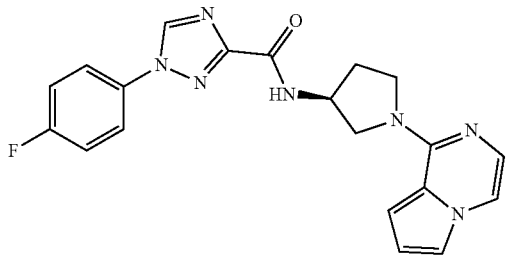

(Compound 7)

or a pharmaceutically acceptable salt thereof.

In some embodiments, the CXCR7 inhibitor has the structure of Compound 8

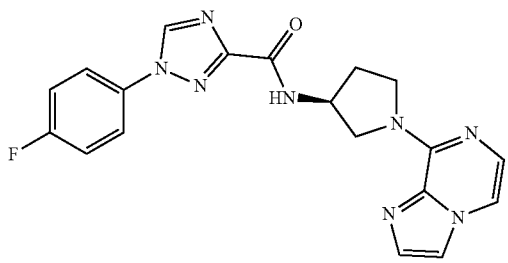

(Compound 8)

or a pharmaceutically acceptable salt thereof.

In some embodiments, the inhibitor of CXCR7 has the structure of Compound 9

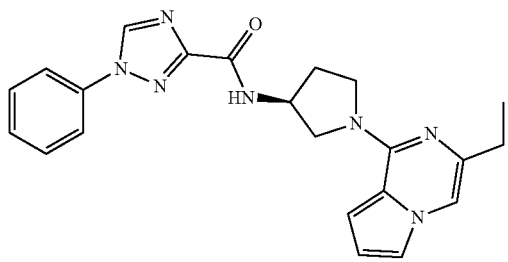

(Compound 9)

or a pharmaceutically acceptable salt thereof.

In some embodiments, the CXCR7 inhibitor is selected from the compounds or pharmaceutical compositions disclosed in PCT publication No. WO2014/085490 stemming from PCT Application No. US2013/072067, filed Nov. 26, 2013 by ChemoCentryx, the content of which is incorporated herein for all purposes.

C. Combination Therapy

The methods of treating cancer disclosed herein can further include one or more additional therapeutic agents.

Additional therapeutic agents that are useful in the present disclosure include compounds or compositions that have anti-cancer activity. In some embodiments, CXCR7 modulators of the present invention can be administered in combination with a chemotherapeutic agents or radiation.

Further examples of other therapeutic agents that may be combined with a compound or composition of the present invention, either administered separately or in the same pharmaceutical compositions, include, but are not limited to: an IGF1 inhibitor (e.g. an antibody or a small molecule), a CXCR4 inhibitor (e.g. AMD3100), an immunomodulatory agent, cisplatin, paclitaxel, methotrexate, cyclophosphamide, ifosfamide, chlorambucil, carmustine, carboplatin, vincristine, vinblastine, thiotepa, lomustine, semustine, 5-fluorouracil and cytarabine. In some embodiments, the one or more additional therapeutic agent may be an anti-IGF1 antibody and/or a CXCR4 inhibitor. In some embodiments, the one or more additional therapeutic agent is a CXCR4 inhibitor. In some embodiments, the one or more additional therapeutic agent is an anti-IGF1 antibody.

There are a number of CXCR4 inhibitors known in the art including small molecules, peptides, and antibodies. Each of these are useful in the present disclosure. A few exemplary CXCR4 inhibitors include AMD3100, as well as the CXCR4 inhibitors provided in WO2007115232, WO2007115231, US20070275965, US20130289020, US20140286936, and US20170226106 the contents of each are incorporated herein for all purposes.

Like CXCR4, a number of small molecule inhibitors and antibodies are known to target IGF1. Exemplary inhibitors include AG538, AG1024, NVP-AEW541 and figitumumab as well as the inhibitors provided in US20090068110, US20140045832, US20050281812, US20050244408, US20120005767, US20140044720, and US20080161278 the contents of each are incorporated herein for all purposes.

The weight ratio of the compound of the present invention to the second active ingredient may be varied and will depend upon the effective dose of each ingredient. Generally, an effective dose of each will be used. Thus, for example, when a compound of the present invention is combined with a second anticancer agent, the weight ratio of the compound of the present invention to the second agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

It is understood that such administration may be prior to, subsequent to or in unison with the second therapeutic agent, such that the therapeutic effects of the second agent are enhanced when compared to administration of the second agent in the absence of the CXCR7 modulator. Selection of the appropriate agents for use in combination therapy may be made by one of ordinary skill in the art, according to conventional pharmaceutical principles. The combination of therapeutic agents may act synergistically, and using this approach, one may be able to achieve therapeutic efficacy with lower dosages of each agent, thus reducing the potential for adverse side effects.

D. Methods of Administration

In general, treatment methods provided herein comprise administering to a patient an effective amount of one or more CXCR7 compounds provided herein. In a preferred embodiment, the compound(s) of the invention are preferably administered to a patient (e.g., a human) orally. Treatment regimens may vary depending on the compound used and the particular condition to be treated; for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

Depending on the cancer to be treated and the subject's condition, the compounds and compositions of the present invention may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration and may be formulated, alone or together, in suitable dosage unit formulations containing conventional nontoxic pharmaceutically acceptable carriers, adjuvants and vehicles appropriate for each rouse of administration. The present invention also contemplates administration of the compounds and compositions of the present invention in a depot formulation.

Dosage levels of the order of from about 0.1 mg to about 140 mg per kilogram of body weight per day are useful (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. A sufficient amount of compounds should be administered to achieve a serum concentration of 50 ng/ml-200 ng/ml.

The compounds and compositions of the present invention can be combined with other compounds and compositions having related utilities to prevent and treat cancer. Such other drugs may be administered, by a route and in an amount commonly used therefor, contemporaneously or sequentially with a compound or composition of the present invention. When a CXCR7 inhibitor is used contemporaneously with one or more other drugs, a pharmaceutical composition containing such other drugs in addition to the CXCR7 inhibitor is preferred. Accordingly, the pharmaceutical compositions of the present invention also include those that also contain one or more other active ingredients or therapeutic agents, in addition to a CXCR7 inhibitor.

The additional therapeutic agent used in the combination therapy—be it a compounds or an antibody antibody may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration. In addition, the compounds and/or antibodies may be formulated, alone or together, in suitable dosage unit formulations containing conventional nontoxic pharmaceutically acceptable carriers, adjuvants and vehicles appropriate for each rouse of administration. The present disclosure also contemplates administration of the compounds and antibodies of the present disclosure in a depot formulation.

It will be understood, that the specific dose level and frequency of dosage for any particular patient may be varied and will depend upon a variety of factors including the activity of the specific compound(s) and/or antibodies employed, the metabolic stability and length of action of that compound, the age, body weight, hereditary characteristics, general health, sex, diet, mode and time of administration, rate of excretion, drug combination, the severity of the particular condition, and the host undergoing therapy.

Combination therapy includes co-administration of the CXCR7 inhibitor and the one or more additional therapeutic agents, sequential administration of the CXCR7 inhibitor and the one or more additional therapeutic agents, or simultaneous administration of separate compositions such that one composition contains the CXCR7 inhibitor and one or more compositions containing the one or more additional therapeutic agents.

Co-administration includes administering the CXCR7 inhibitor of the present disclosure within 0.5, 1, 2, 4, 6, 8, 10, 12, 16, 20, or 24 hours of the one or more administration of the one or more additional therapeutic agents. Moreover, the CXCR7 inhibitor and one or more additional therapeutic agents can each be administered once a day, or two, three, or more times per day so as to provide the preferred dosage level per day.

IV. Examples

The following examples are offered to illustrate, but not to limit, the claimed invention.

Figure 1C:
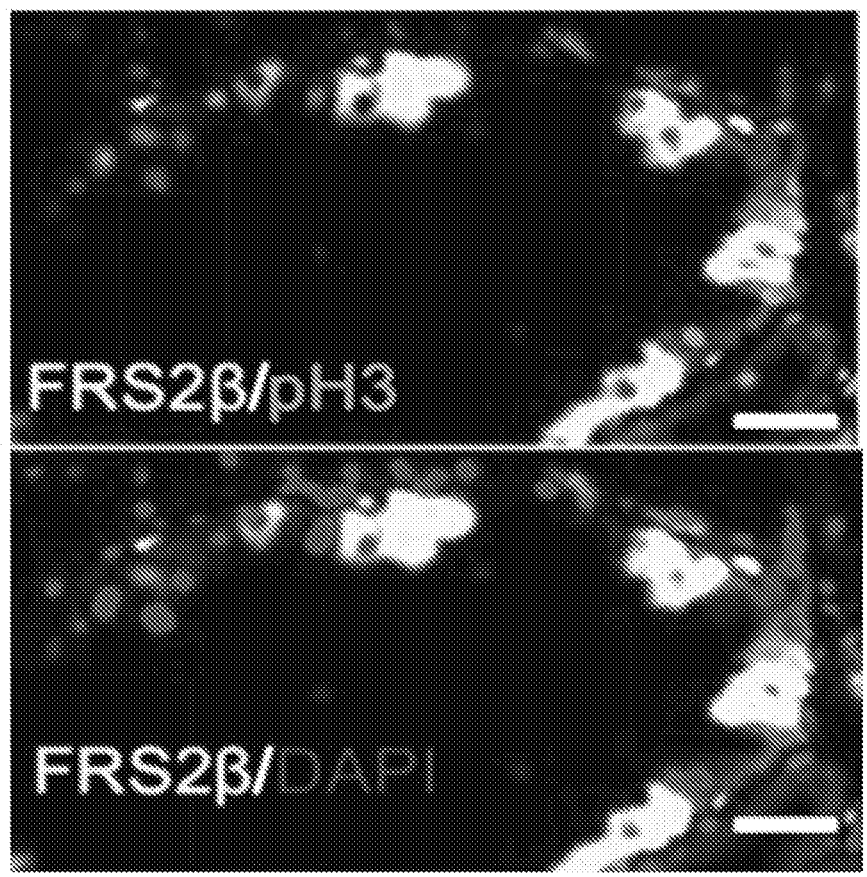
Figure 1D:
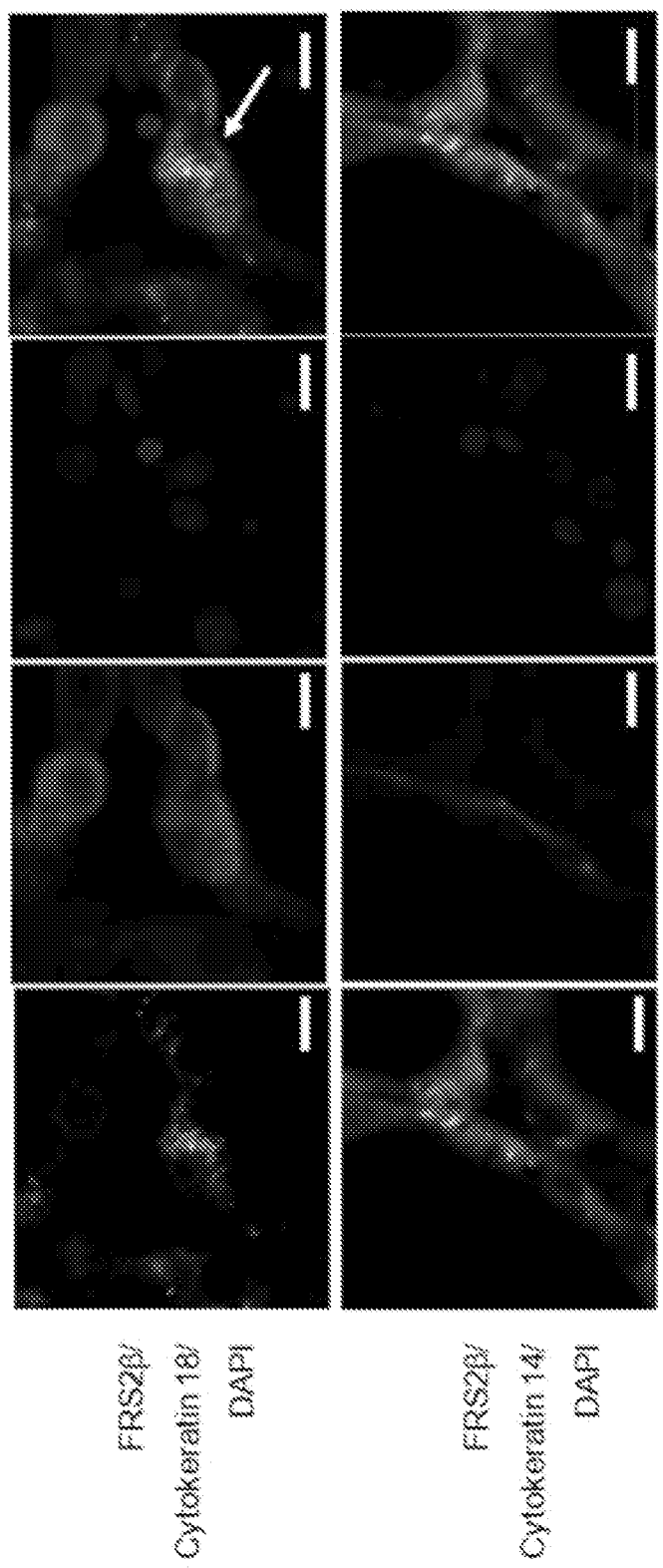

Example 1: FRS2β Expressed in Luminal Progenitor Cells Creates the Microenvironment Favorable for Mammary Tumorigenesis To examine the role of FRS2β in vivo, we mutated Frs2β gene in mice by gene targeting. The mutant mice grew normally and were fertile with no gross abnormality. The promoter activity of Frs2β was detected by the β-galactosidase staining of the mature female mammary tissues, which were heterozygous for the Frs2β mutant allele (FIG. 1A). The amount of Frs2β transcripts were significantly increased during pregnancy and lactation, then after weaning (3 weeks after birth), it decreased during the regression period (data not shown). By immunohistochemistry, we confirmed that FRS2β is expressed in a few cells in the lobules of the mammary gland (FIG. 1C). Most FRS2β-positive cells were negative for phospho-histone H3, a nucleus marker for dividing cells, indicating that they proliferate more slowly than others, consistent with the negative role of FRS2β in cell proliferation (FIG. 1C). FRS2β was expressed in a few cells which were positive for cytokeratin 18 (luminal cell marker), but not for cytokeratin 14 (myoepithelial cell marker) (FIG. 1D). These data indicate that a small number of luminal cells in mammary gland express FRS2β. On the other hand, whole-mount staining of the mammary gland showed no gross structural abnormality in the mutant mice. This led us to examine the pathological role of FRS2β in tumorigenesis.

Figure 1E:
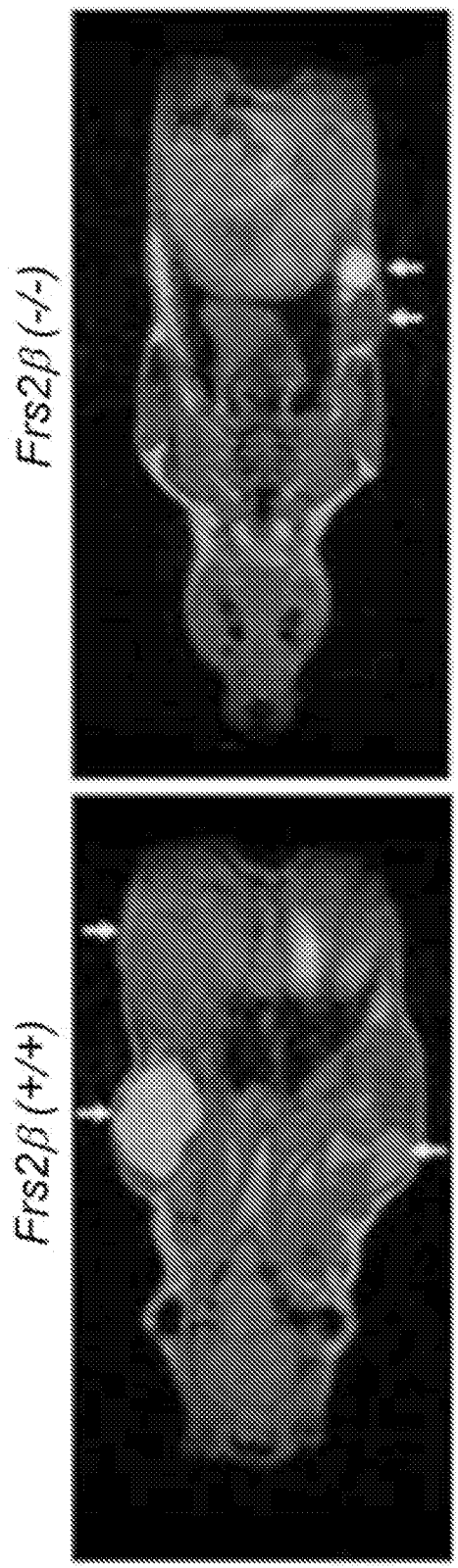
Figure 1F:
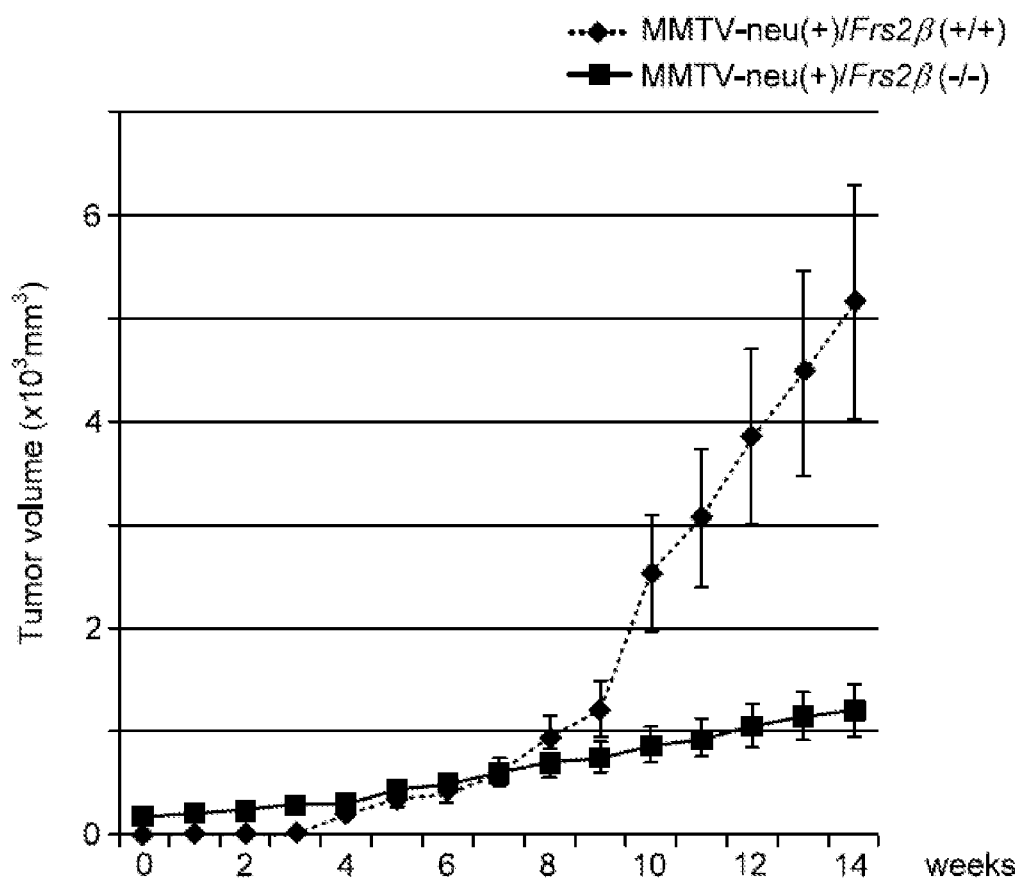
Figure 1G:
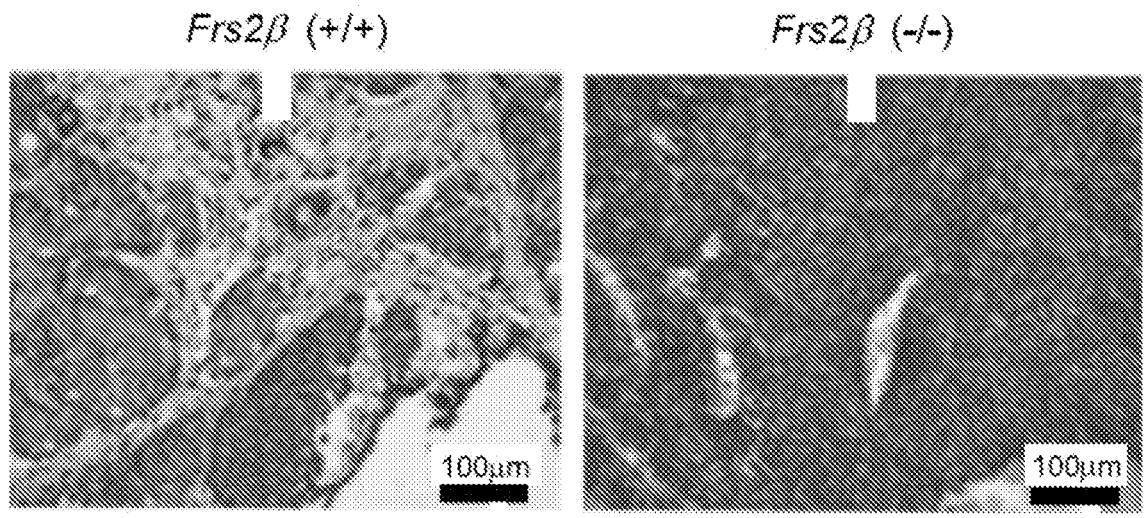

We crossed the Frs2β mutant mice with MMTV-neu (+) mice to generate the MMTV-neu (+)/Frs2β (+/+) mice and MMTV-neu (+)/Frs2β (−/−) mice, hereafter referred to as Frs2β (+/+) and Frs2β (−/−) mice, respectively. We observed that the tumorigenesis began earlier with higher probability in MMTV-neu (+) mice that had experienced pregnancy at ~8-week old (23.4+1.9 weeks, 83%, n=8) than in virgin MMTV-neu (+) mice (32.6+2.6 weeks, 23.4%, n=8). We thus examined the tumorigenesis in the mice immediately after pregnancy and lactation. We used nuclear magnetic resonance (NMR) imaging which is a sensitive method to detect tumors even with 1 mm diameter[20] (FIG. 1E). We began to observe small tumors after 5~8 weeks after measurement started and found that the tumor growth rate was much lower in the Frs2β (−/−) mice than in the Frs2β (+/+) mice (FIGS. 1E, 1F), while the tumor incidence showed a similar rate, 83.2% (n=18) in Frs2β (+/+) and 88.2% (n=17) in Frs2β (−/−). This result indicates that FRS2β plays important roles in mammary tumorigenesis. To examine the molecular mechanisms, we initially compared the tumor histology. There was ample amount of stroma in the Frs2β (+/+) tumors, reminiscent of the human breast cancer tissues (FIG. 1G). However, it was much less in the Frs2β (−/−) tumors. Considering the fact that tumor stroma is a major component of the tumor microenvironment, we hypothesized that FRS2β may play roles in creating the favorable microenvironment for tumorigenesis in mammary tissues.

Figure 1H:
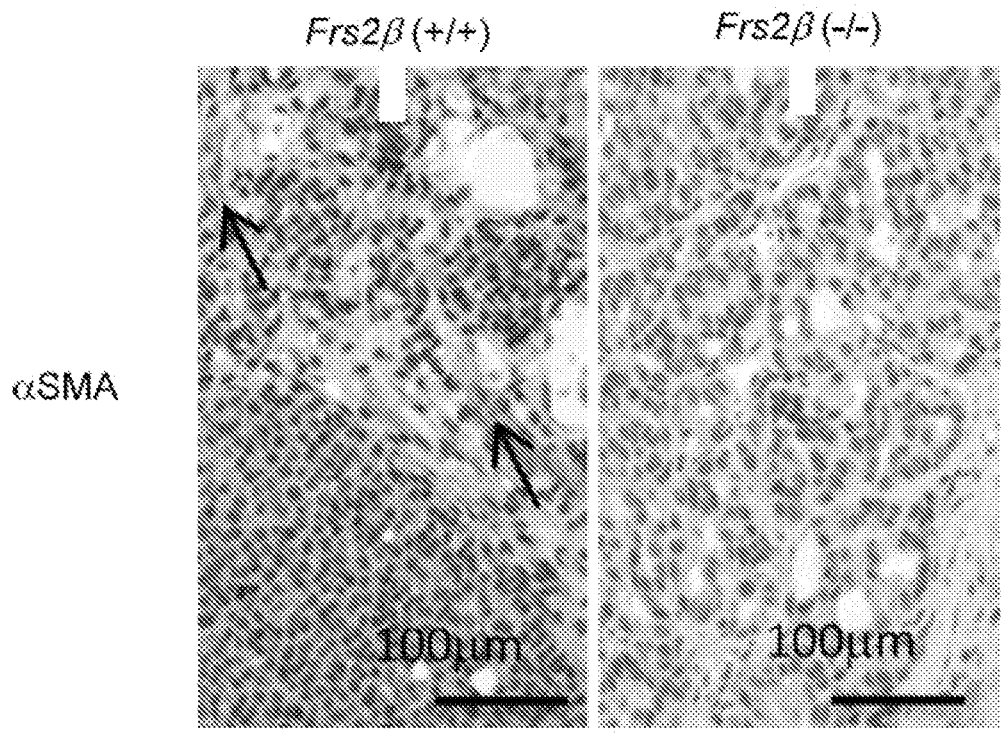

Histological examination revealed that Frs2β (+/+) tumors contained ample stroma, reminiscent of human breast cancer tissues (arrows in FIG. 1G). By contrast, very little stroma was observed in Frs2β (−/−) tumors. High levels of smooth muscle actin (SMA)-positive CAFs were present in the stroma of Frs2β (+/+) tumors, but not in Frs2β (−/−) tumors (arrows in FIG. 1H). These results indicate that FRS2β is required for formation of tumor stroma.

Figure 2A:
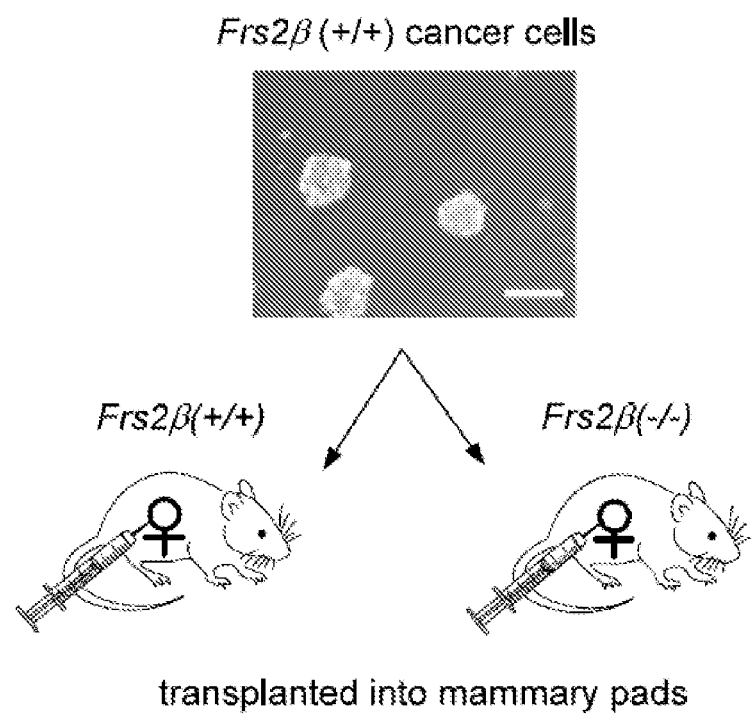
FIG. 2A-F FRS2β expressed in luminal progenitor cells supports tumorigenesis derived from xenografted tumor cells (A) Frs2β (+/+) tumor sphere cells cultured for 14 days as shown by the representative image were inoculated into Frs2β (+/+) or Frs2β (−/−) 8-weeks old virgin female mouse mammary fat pads. (B) Representative tumors were photographed at 30 days after transplantation, and (C) tumor volues of the removed tumors were measured. (D) Tumorigenesis derived from Frs2β (+/+) tumor sphere cells was observed in Frs2β (+/+) mice but not in Frs2β (−/−) mice (n=4). The numbers indicate the ratio of numbers of tumors to the numbers of the inoculated sites. (E) Immunohistochemial staining for MMTV-neu (−) or MMTV-neu (+) female mammary glands by anti-FRS2β antibody and anti-ErbB2 antibody. Arrows indicate the FRS2β-positive luminal cells. (F) Mammary epithelial cells were sorted by using the markers. Subpopulations of P1 (CD49f$_{low}$/CD24$_{high}$) luminal cells were further sorted by using CD61. Subpopulations of P2 (CD49f$_{low}$/CD24$_{high}$/CD61+) luminal progenitor cells were further sorted by FRS2β to obtain subpopulation of P3 (CD49f$_{low}$/CD24$_{high}$/CD61+/FRS2β+).
Figure 2B:
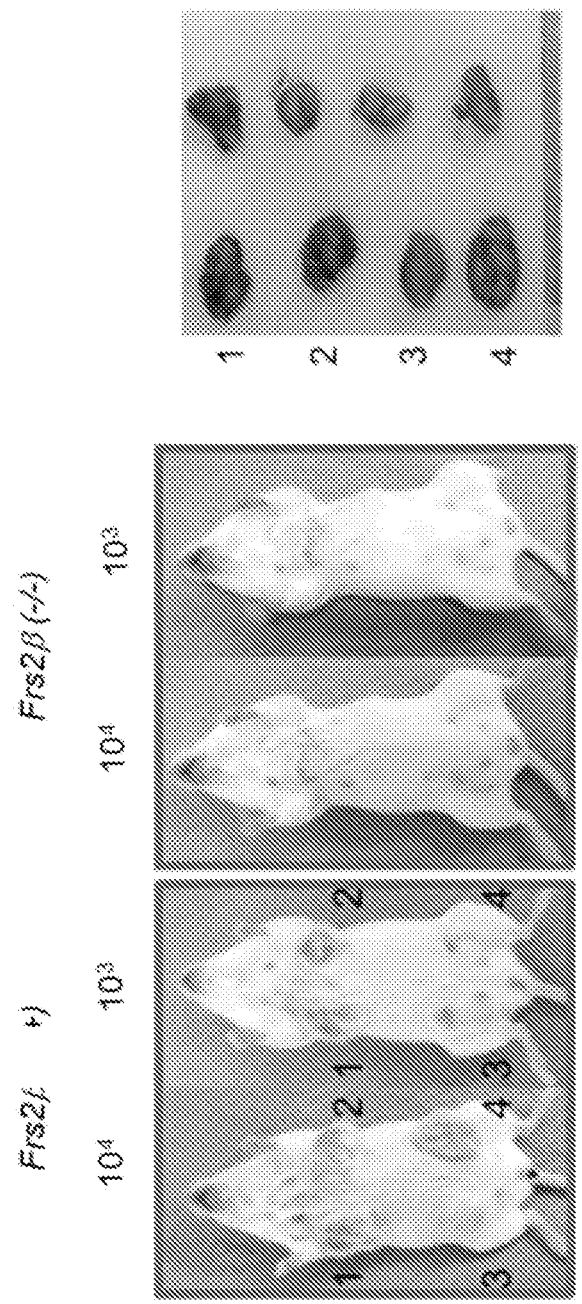
Figures 2C, 2D:
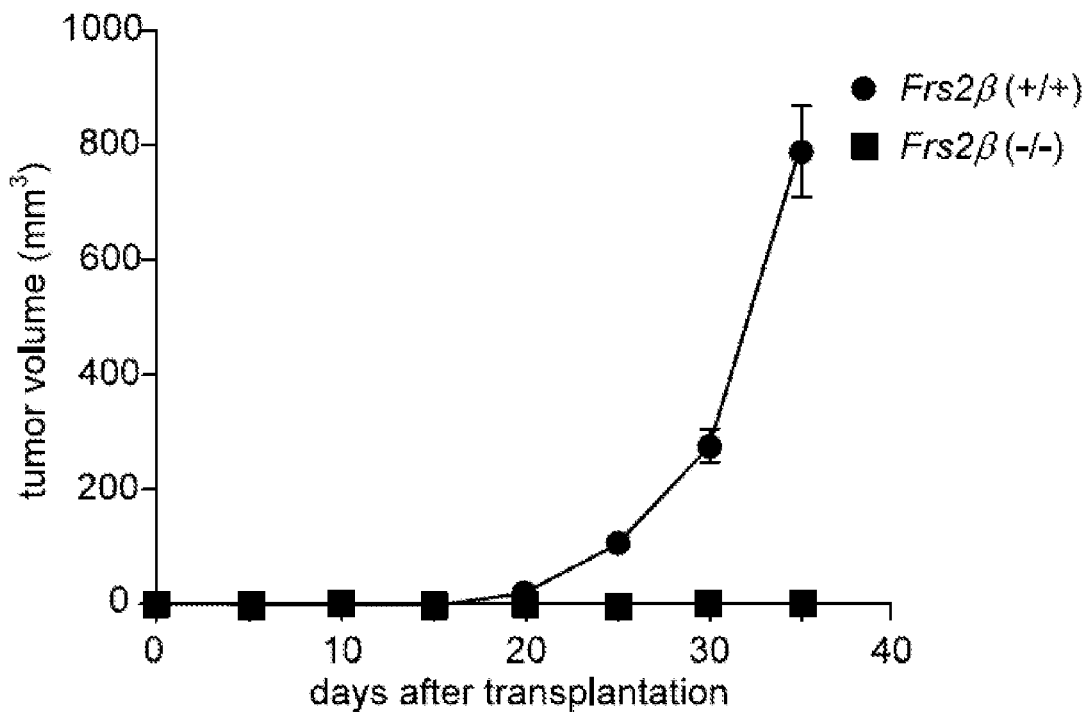

Testing the idea that FRS2β plays roles in creating the mammary tissue microenvironment required for tumorigenesis, even before tumor onset, we performed xenograft experiments in which Frs2β (+/+) tumor cells were inoculated into young virgin precancerous mammary tissues of Frs2β (+/+) and Frs2β (−/−) mice. We cultured Frs2β (+/+) tumor cells in a serum-free suspension condition, as spheres to enrich for $CSC_{S15,21}$. We then inoculated them into the Frs2β (+/+) or Frs2β (−/−) 8-week old virgin mammary tissues after limiting dilution and measured the tumorigenesis (FIG. 2A). Intriguingly, tumors were formed only in Frs2β (+/+) but not in Frs2β (−/−) mammary tissues, and rapidly grew within 1 month (FIGS. 2B, 2C, 2D). This result suggests that the CSCs disappeared in the Frs2β (−/−) microenvironment in mammary tissues. As expected, tumors were not formed when Frs2β (+/+) tumor cells were inoculated into the Frs2β (+/+) male mammary fat pads (data not shown), confirming that the mammary tissues are important for tumorigenesis. Therefore, precancerous mammary cells expressing FRS2β appear to create the microenvironment that supports growth of CSCs and allows tumorigenesis.

Figure 2E:
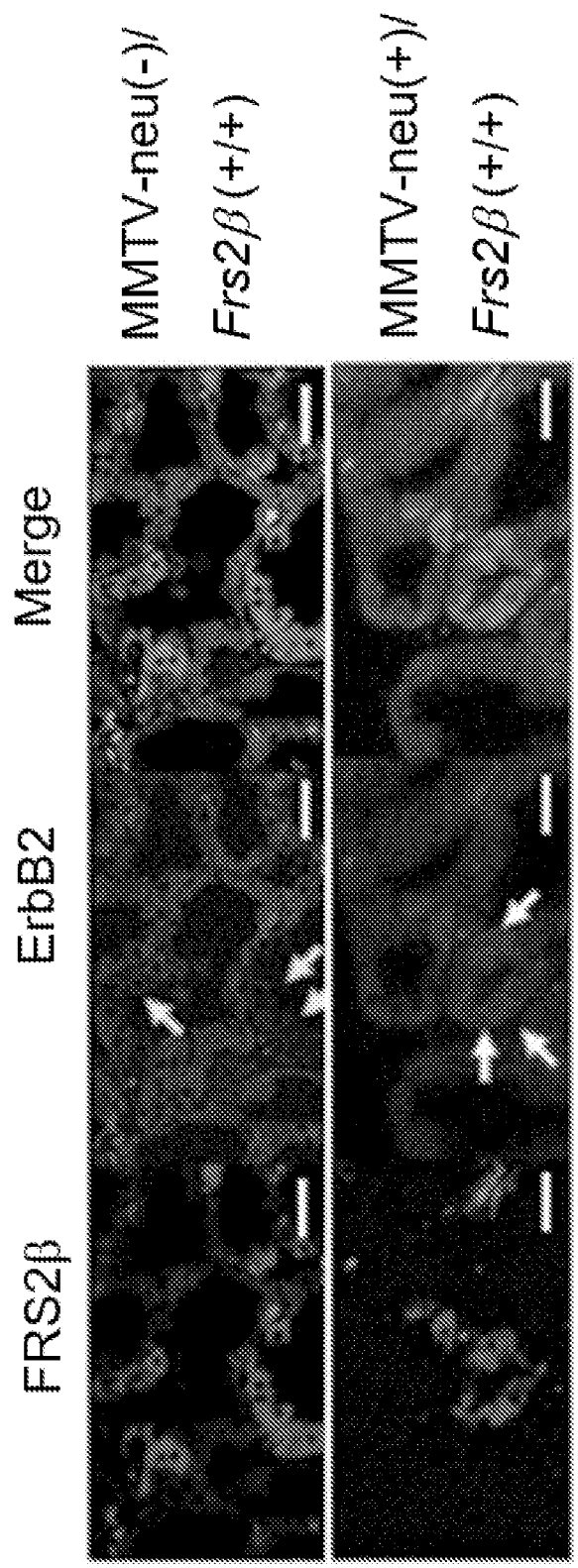
Figure 2F:
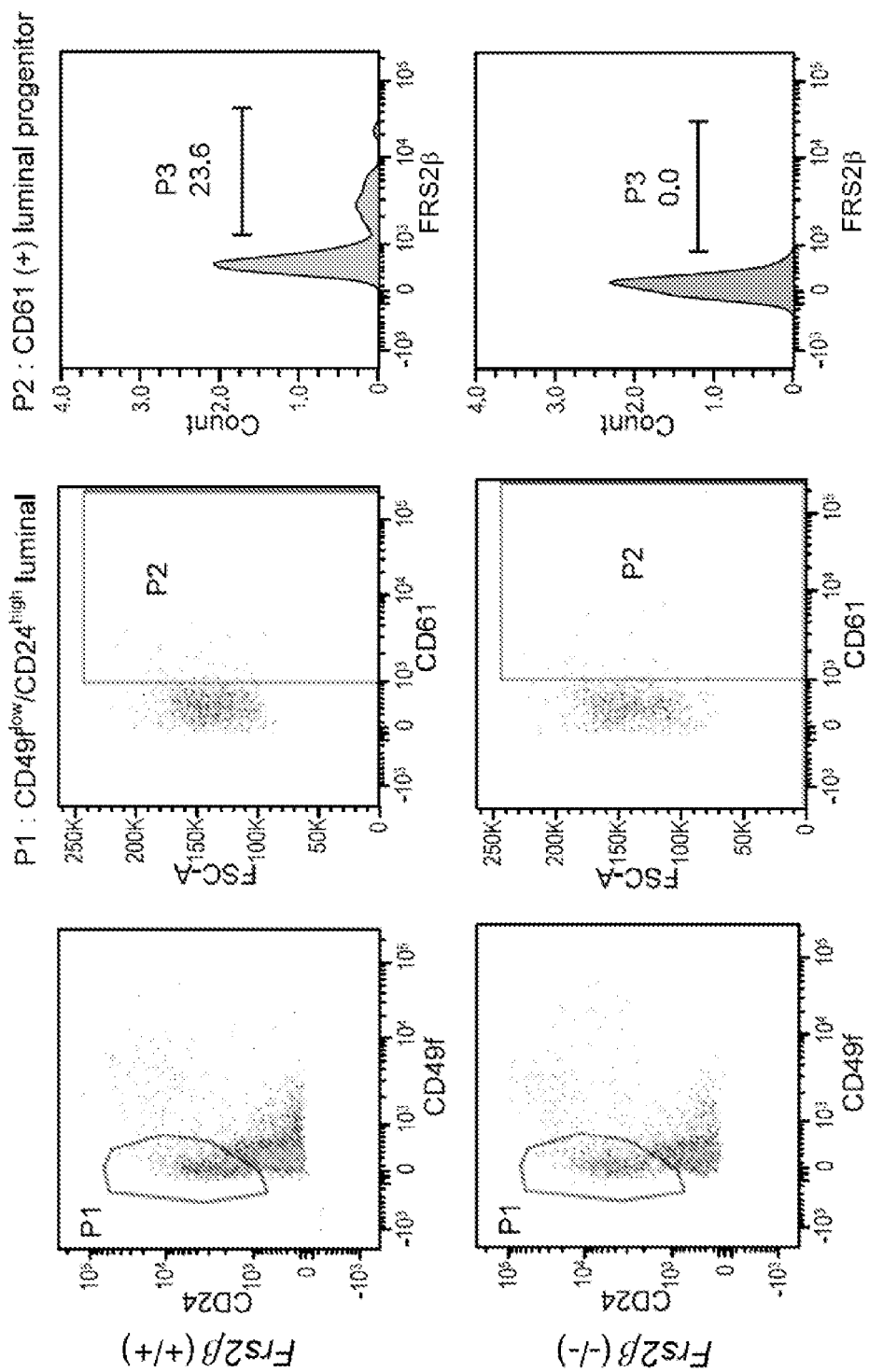

By immunohistochemistry, we found that there are similar numbers of luminal cells expressing FRS2β in MMTV-neu (−) mice and MMTV-neu (+) mice (FIG. 2E). The endogenous ErbB2 expression was modestly decreased in the FRS2β-positive cells in the MMTV-neu (−) mice (yellow arrows), consistent with the fact that FRS2β is involved in ubiquitylation and degradation of $ErbB2_{19}$; whereas ErbB2 was overexpressed in the FRS2β-positive cells in the MMTV-neu (+) mice (white arrows). To further examine in which type of luminal cells FRS2β is expressed, we sorted the mammary cells by using surface markers. It is known that the luminal cells are enriched in the $CD49f_{low}/CD24_{high}$ cell population[22] and that the luminal progenitor cells can be enriched by further fractionation with CD61 for the $CD49f_{low}/CD24_{high}/CD61_+$ population[23]. Significant expression of FRS2β was observed in 23.6% cells among the $CD49f_{low}/CD24_+high/CD61+$ luminal progenitor cell population (FIG. 2F). We confirmed that FRS2β was lost in CD49flow/CD24high/CD61+ luminal progenitor cell population derived from Frs2β (−/−) mammary cells. These data suggest that a subset of luminal progenitor cells in the mammary gland express FRS2β.

Figure 3A:
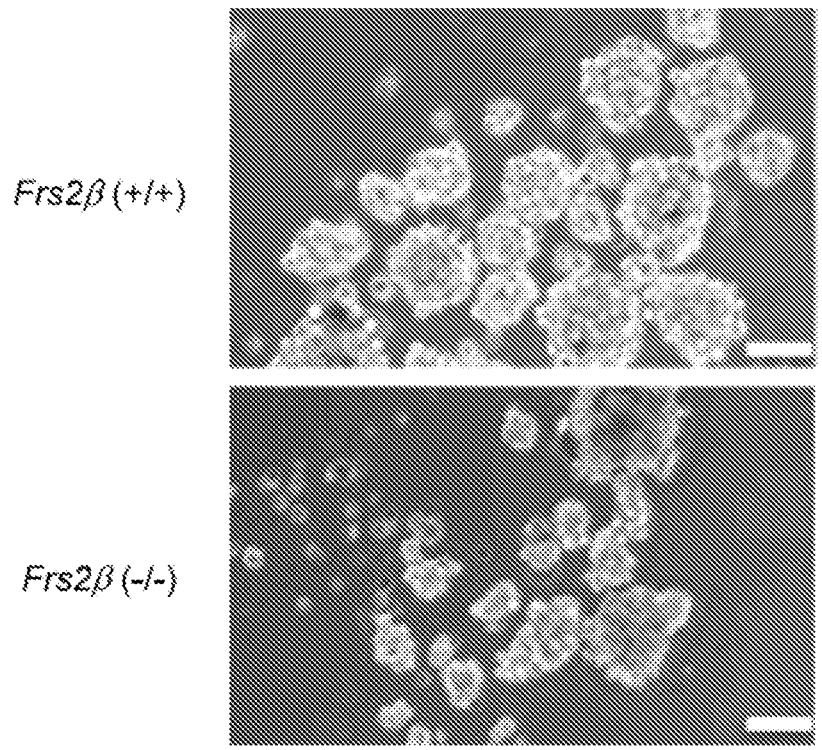
FIG. 3A-F FRS2β deficient luminal progenitor cells produce less amounts of cytokines (A) Representative images of mammospheres derived from Frs2β (+/+) and Frs2β (−/−) mammary epithelial cells cultured in sphere culture medium (SCM). (B) Quantification of the sphere forming efficiency of mammosphere cells. N.T., not treated by cytokines-cocktail in SCM. Results were shown as mean±SEM. n=4. **p<0.01, *p<0.05. (C) Gene set enrichment analysis (GSEA) was used to compare gene expression profiles in Frs2β (+/+) and Frs2β (−/−) mammosphere cells. Two gene sets, highly upregulated in Frs2β (+/+) mammosphere cells are shown. (D) Gene set enrichment analysis (GSEA) was used to compare gene expression profiles in Frs2β (+/+) and Frs2β (−/−) precancerous mammary epithelial cells. Gene sets highly upregulated in Frs2β (+/+) cells or Frs2β (−/−) cells are shown. ES, enrichment score; NES, normalized enrichment score; FDR, false discovery ratio. (E) Expression levels of indicated gene transcripts were compared between Frs2β (+/−) and Frs2β (−/−) mammosphere cells by using real-time quantitative PCR (qPCR). Results were shown as mean±SEM. n=4. **p<0.01. (F) Immunohistochemical staining for Frs2β (+/+) and Frs2β (−/−) mammary tumors using antibodies against αSMA, CXCL12 and IGF1.
Figure 3B:
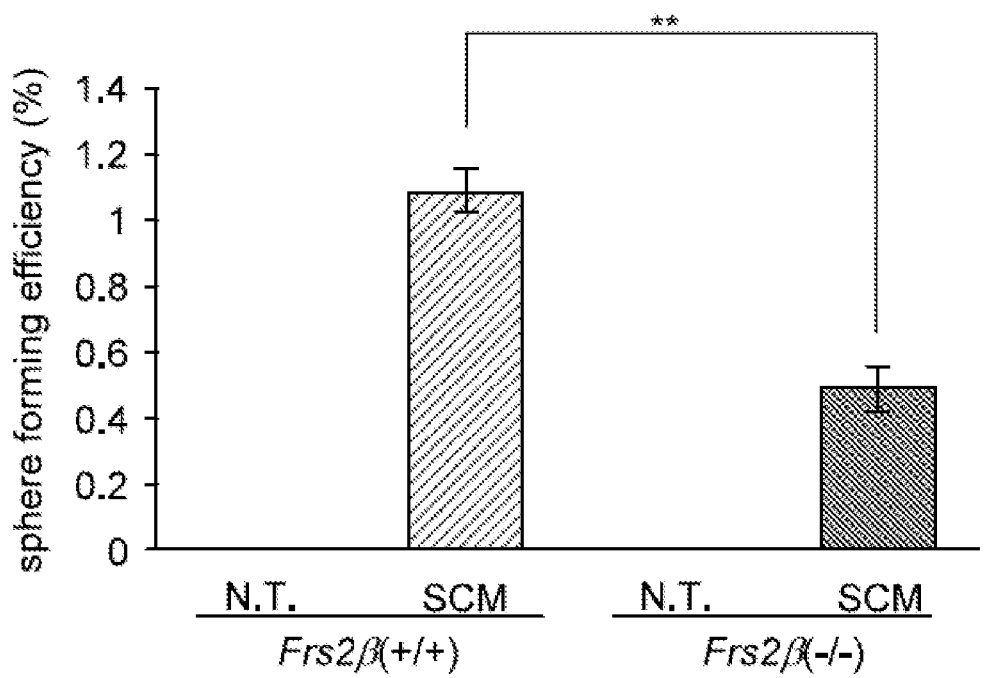
Figure 3C:
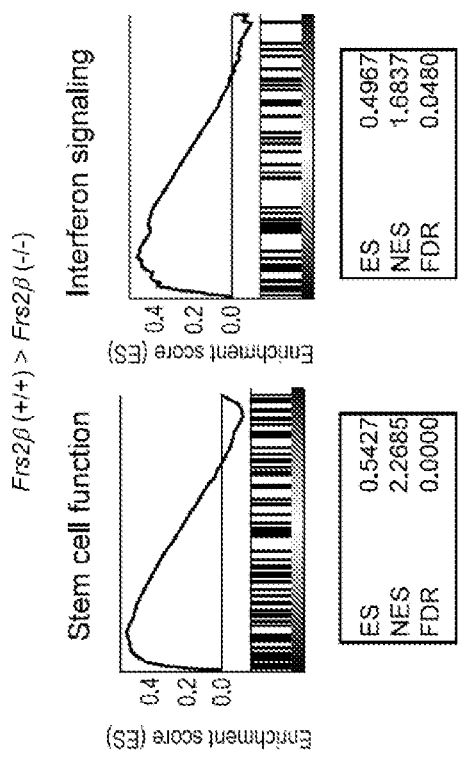
Figure 3D:
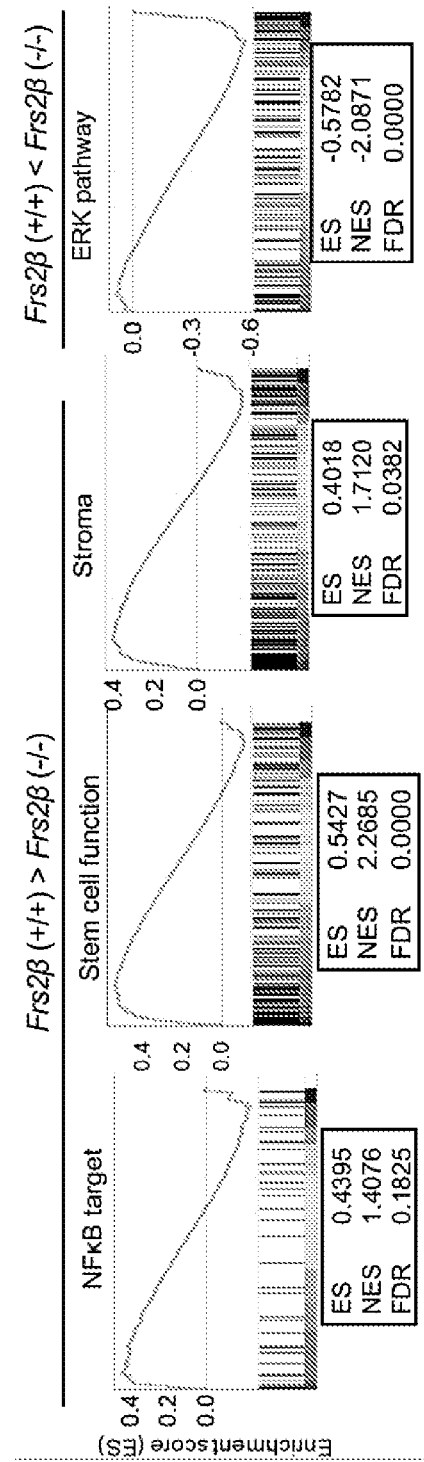

Example 2: Precancerous Mammary Cells Express Cytokines that are Dependent on FRS2β Expression We next examined the molecular mechanisms by which FRS2β expressed in the luminal progenitor cells creates the microenvironment that is favorable for tumorigenesis. We cultured Frs2β (+/+) or Frs2β (−/−) precancerous mammary cells in a serum-free suspension condition to enrich for the undifferentiated or progenitor cells as spheres and measured their mammosphere forming ability (FIGS. 3A and 3B). We dissociated these primary spheres to single cell suspension and cultured them to generate the secondary mammospheres. It is thought that the secondary spheres accurately reflect the incidence of sphere-forming, undifferentiated or progenitor cells. We found that the deficiency of FRS2β led to significantly lower sphere forming ability (FIGS. 3A, 3B). There was no significant difference in the diameter of mammospheres, suggesting that the proliferation rate was similar between Frs2β (+/+) and Frs2β (−/−) precancerous mammary cells. To examine which functions of luminal progenitor cells are disrupted by the loss of FRS2β, we compared the transcriptomic profiles between Frs2β (+/+) and Frs2β (−/−) mammosphere cells by using DNA microarray. Gene set enrichment analysis (GSEA) showed that the stem cell function-related gene set and the interferon signal-related gene set were enriched in Frs2β (+/+) mammosphere cells, compared to the Frs2β (−/−) cells (FIG. 3C). GSEA in precancerous mammary epithelial cells also revealed that gene sets related to NFkB targets, stem cell function, and stroma were enriched in Frs2β (+/+) cells relative to Frs2β (−/−) cells (FIG. 3D). The ERK pathway-related gene set was upregulated in Frs2β (−/−) cells relative to Frs2β (+/+) cells, which was expected because FRS2β inhibits ERK signaling. Many genes encoding cytokines were upregulated in Frs2β (+/+) cells; among them, 18 genes were expressed at >1.5-fold higher levels in Frs2β (+/+) cells than in Frs2β (−/−) cells (data not shown).

Figure 3E:
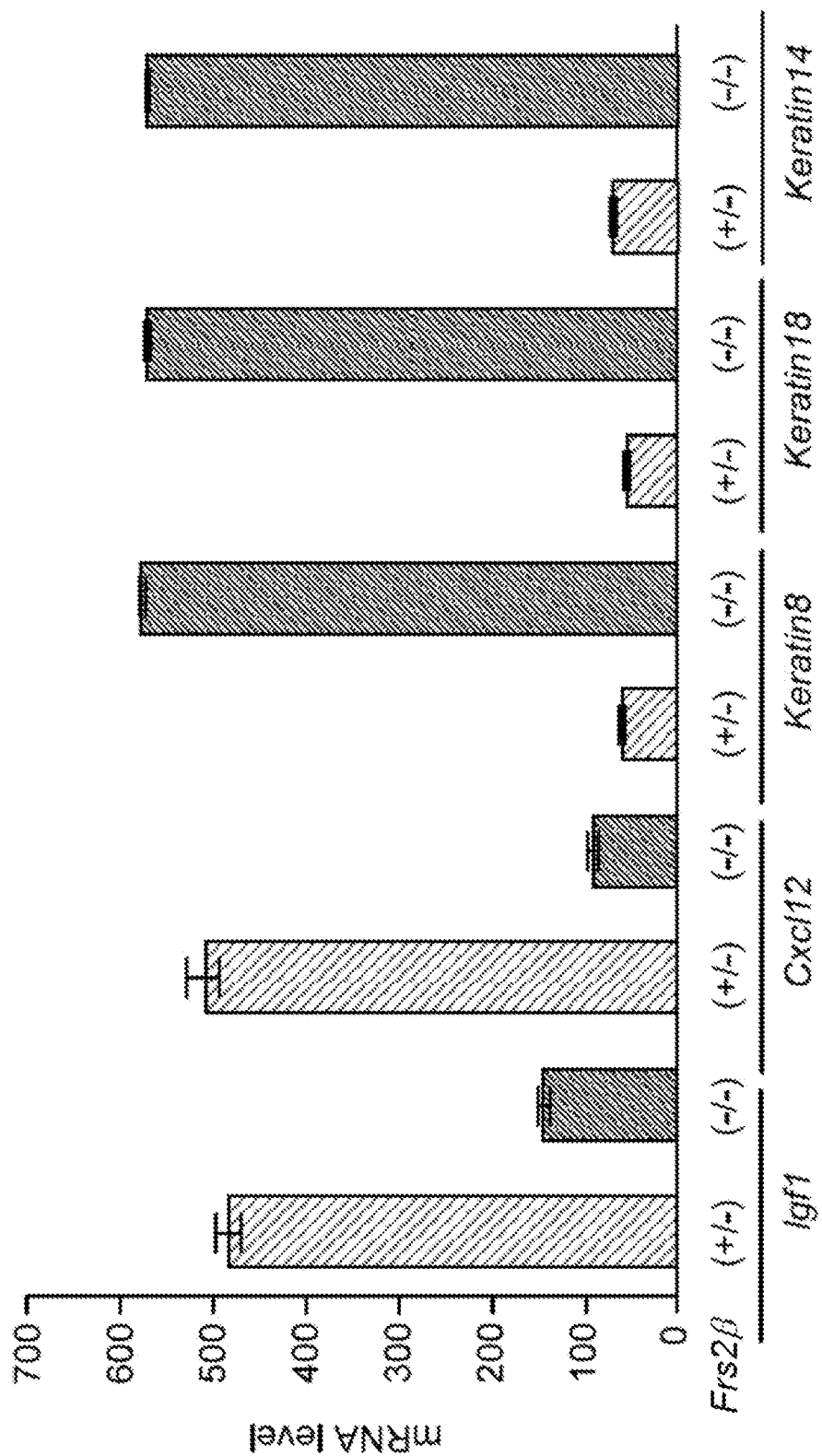
Figure 3F:
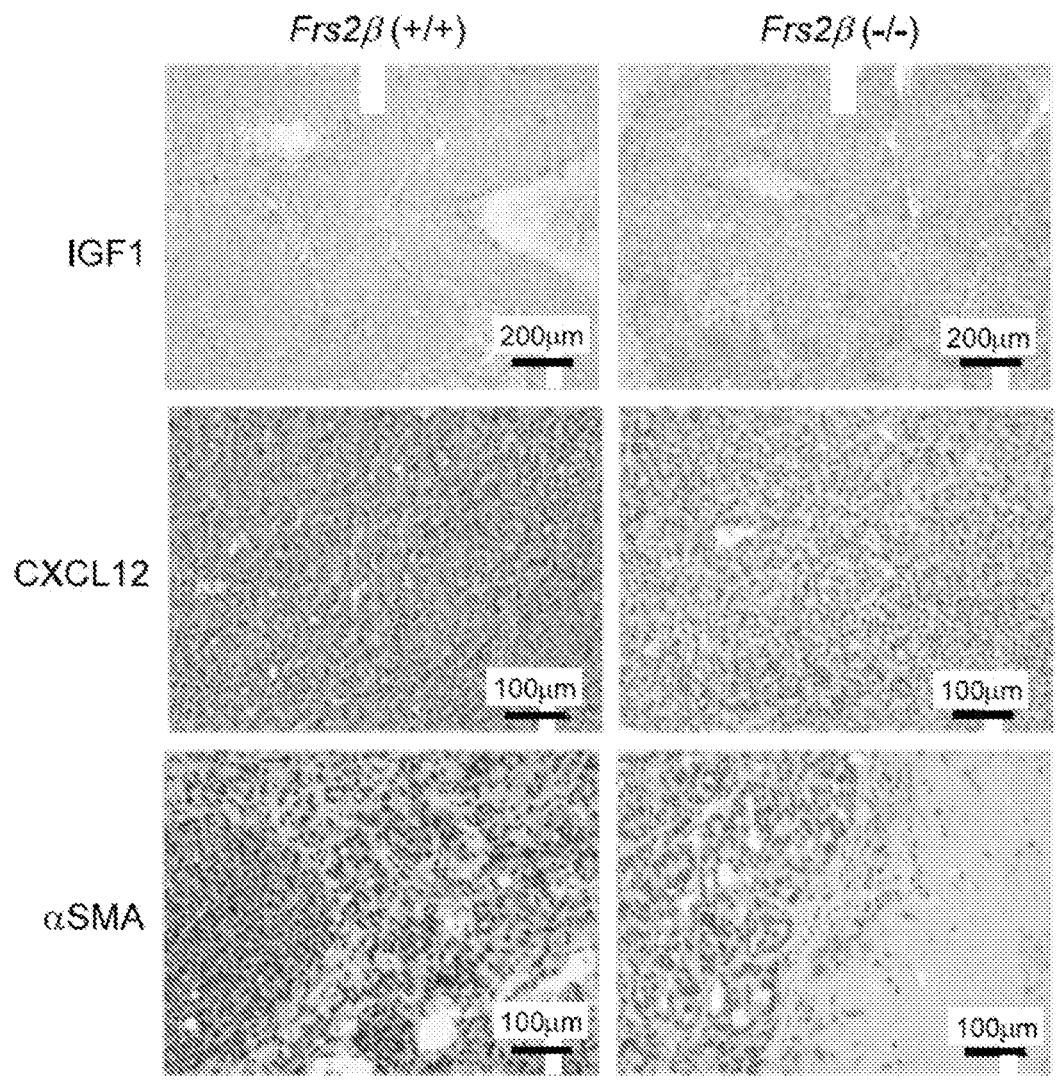

Then, we focused on IGF1, which is included in the stem cell function-related gene set, and CXCL12, which is included in the interferon signal-related gene set and the stroma-related gene set, among the top genes that were highly expressed in the Frs2β (+/+) cells. Quantitative PCT (qPCT) confirmed that Igf1 and Cxcl12 transcripts were expressed strongly in the heterozygote Frs2β (+/−) mammary cells than in the Frs2β (−/−) cells, while the differentiated cell markers (Keratin8, Keratin18 and Keratin14) were upregulated in the Frs2β (−/−) cells (FIG. 3E). By immunohistochemistry, we confirmed that the protein levels of IGF1, CXCL12, and αSMA, a CAF marker, were greater in the Frs2β (+/+) mammary tissues (FIG. 3F). The strong staining with αSMA confirmed the mobilization of CAFs in the wild type mammary tissues.

Figure 4A:
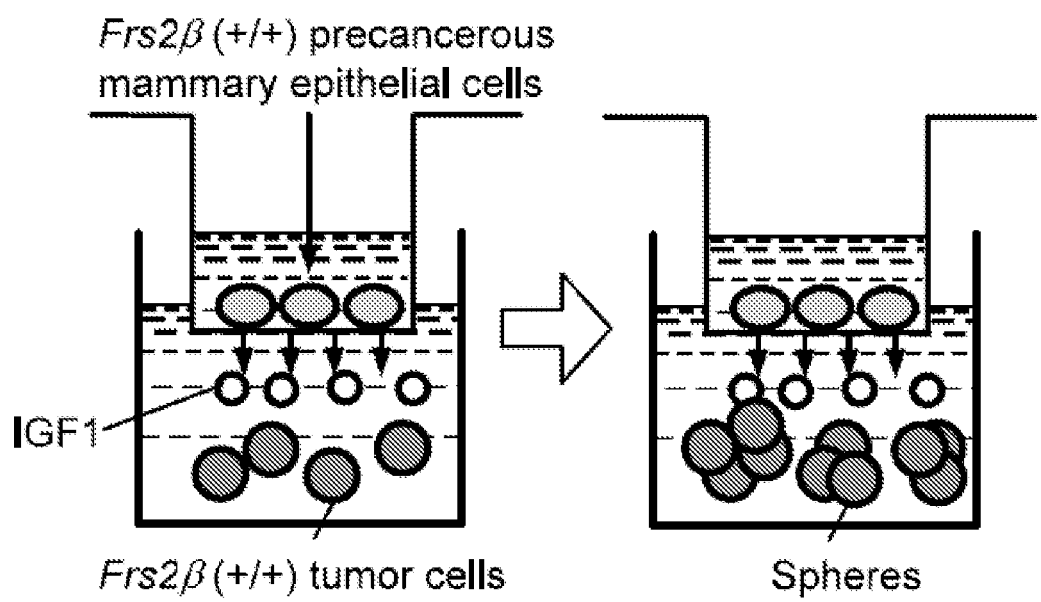
FIG. 4A-I CXCL12 produced from precancerous Frs2β (+/+) mammary cells induce tumor spheres and migration of CAFs. (A) Schematic of co-culture of Frs2β (+/+) tumor cells to form spheres in the lower chamber with Frs2β (+/+)
Figure 4B:
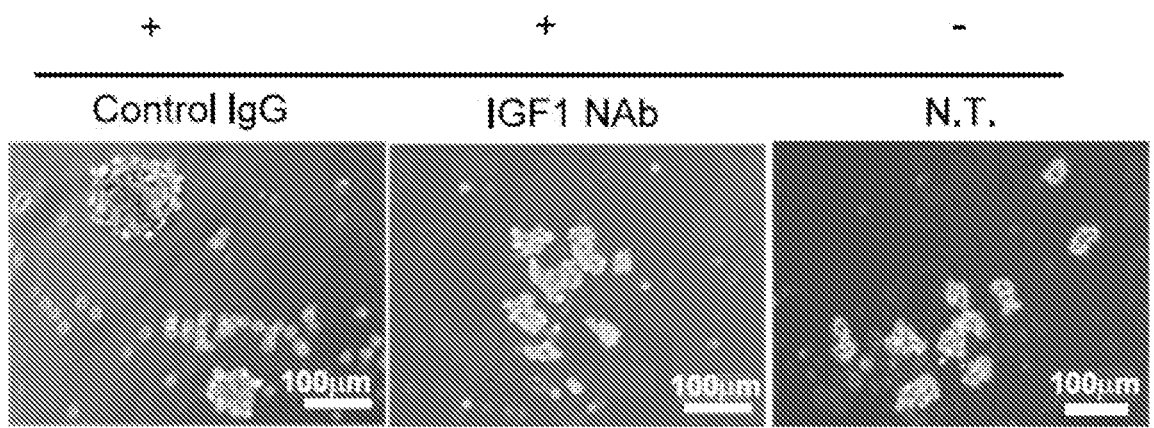
Figure 4C:
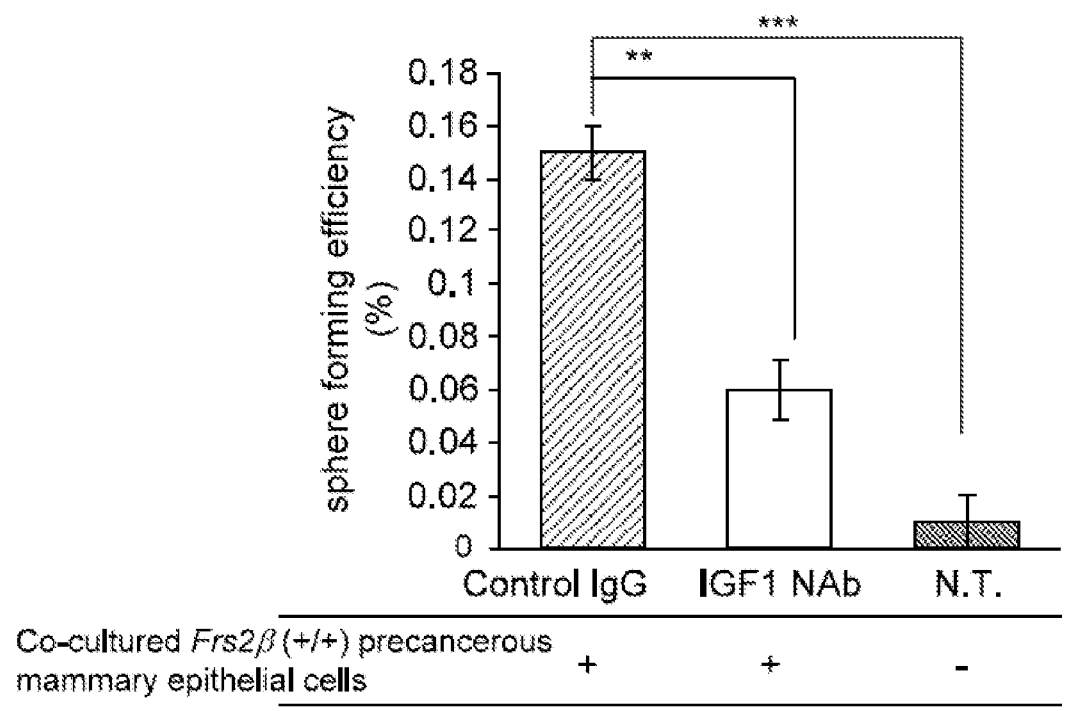

Example 3: FRS2β-Dependent Increase in Production of CXCL12 in Precancerous Mammary Cells Allows Tumorigenesis Treatment with a CXCR7 Inhibitor or a CXCR7 Inhibitor in Combination with Another Therapeutic Agent Modulates Tumor Growth Tumor sphere formation reflects the properties of CSCs, whose growth is dependent on cytokines in the culture. To determine whether IGF1 derived from precancerous mammary epithelial cells plays a role in tumor sphere formation, we cultured Frs2β (+/+) tumor cells under serum-free suspension condition without the cytokine cocktail in the presence or absence of Frs2β (+/+) precancerous mammary epithelial cells (FIG. 4A). We observed tumor sphere formation by Frs2β (+/+) tumor cells in the presence of Frs2β (+/+) precancerous mammary epithelial cells, but not in their absence (compare control IgG vs. not treated [N.T.] in FIGS. 4B and 4C). Treatment with an IGF1 neutralizing antibody (IGF1 NAb) greatly diminished tumor sphere formation by Frs2β (+/+) tumor cells co-cultured with Frs2β (+/+) precancerous mammary cells (FIGS. 4B and 4C). These findings indicate that IGF1 derived from nearby Frs2β (+/+) precancerous mammary epithelial cells plays an important role in tumor sphere formation. Thus, IGF1 derived from Frs2β (+/+) precancerous mammary epithelial cells may support CSC growth.

Figure 4D:
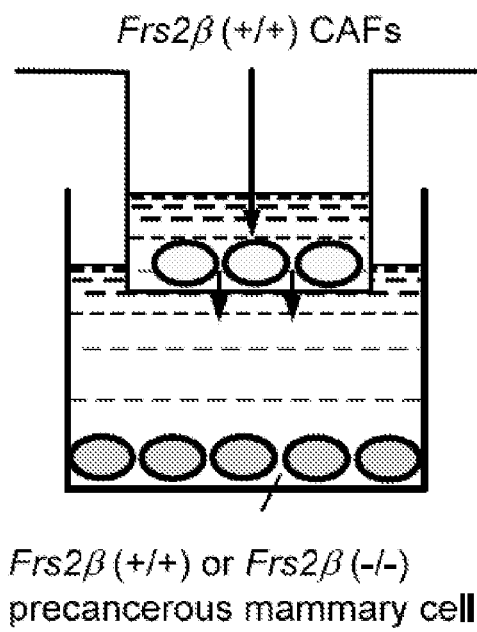
Figure 4E:
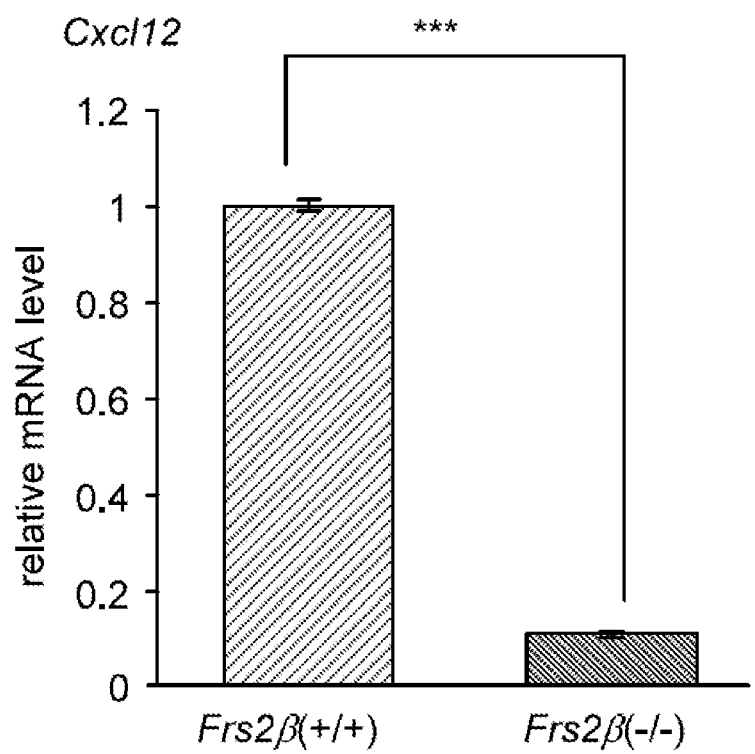
Figure 4F:
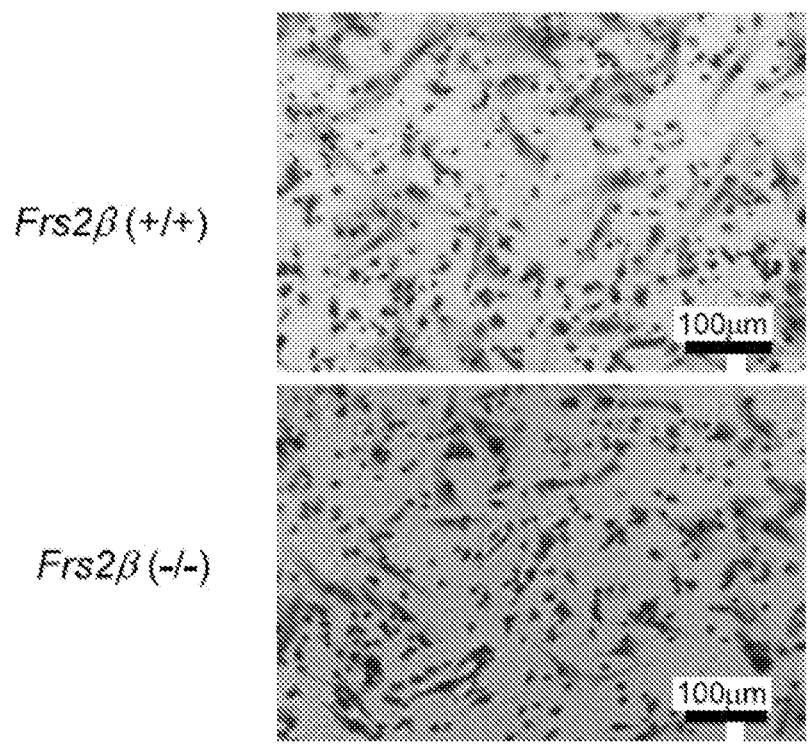
Figure 4G:
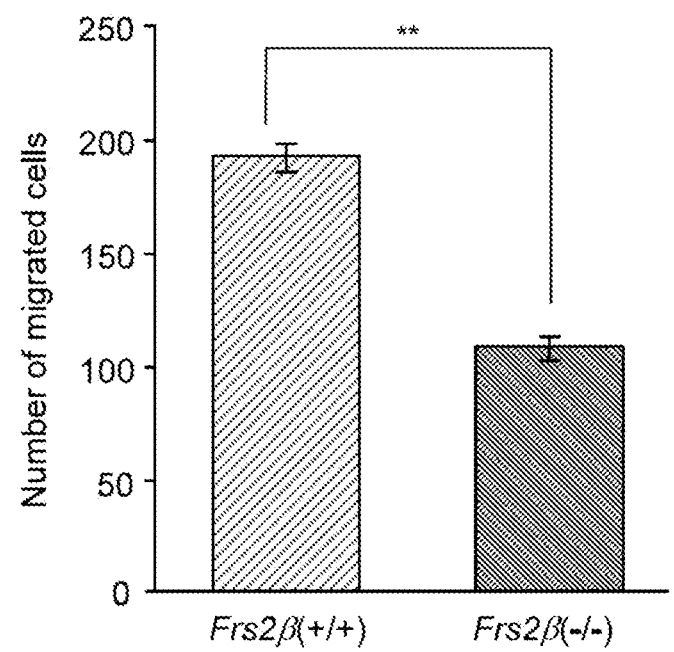
Figure 4H:
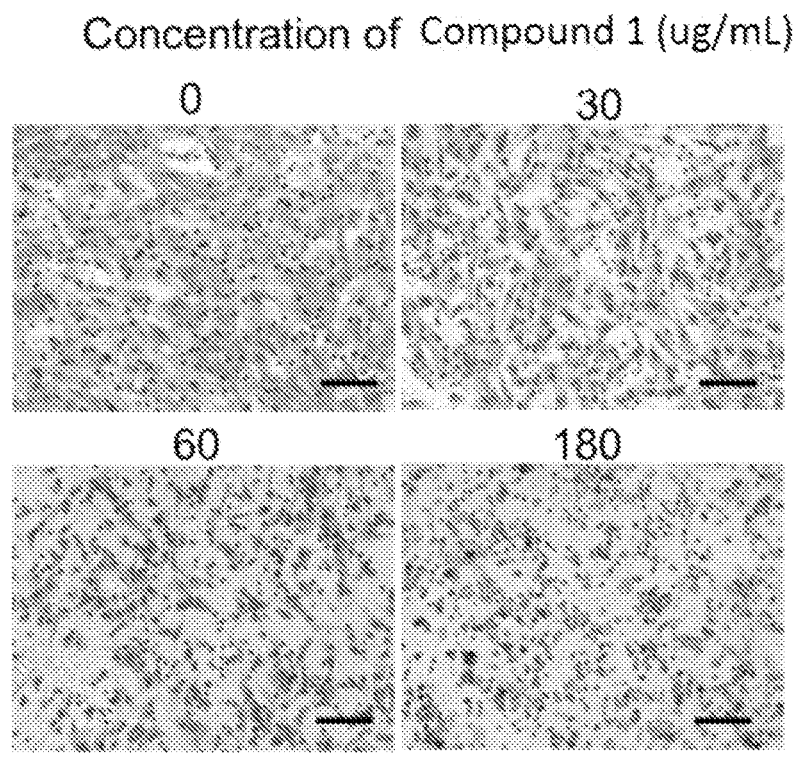
Figure 4I:
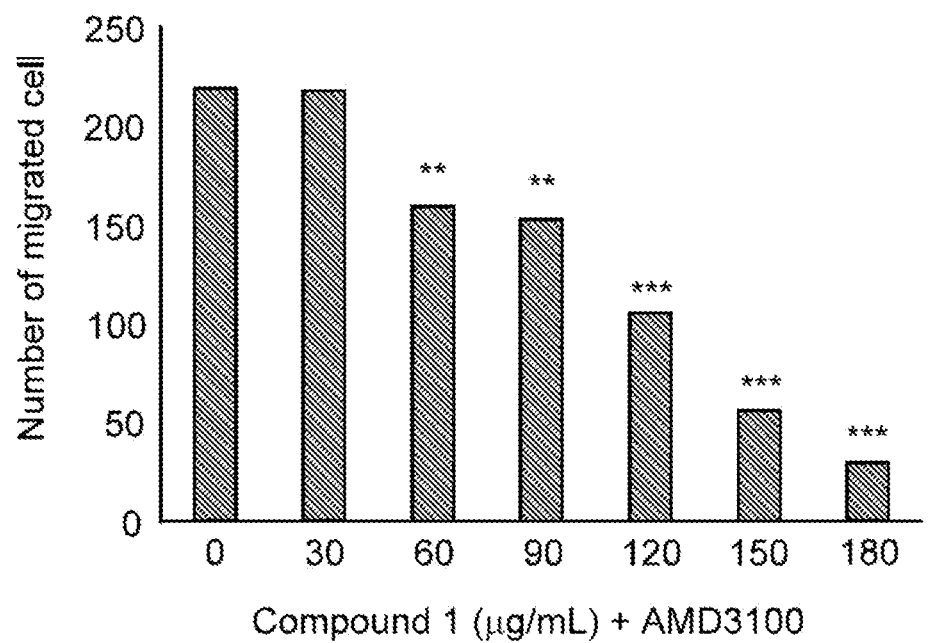

To examine whether CXCL12 derived from precancerous mammary epithelial cells plays roles for cancer-associated fibroblasts (CAFs), we co-cultured Frs2β (+/+) CAFs with Frs2β (+/+) or Frs2β (−/−) precancerous mammary epithelial cells (FIG. 4D). We confirmed that the expression levels of Cxcl12 were higher in this culture condition in the Frs2β (+/+) precancerous mammary cells, than in the Frs2β (−/−) cells (FIG. 4E). We observed significantly more migrated CAFs when co-cultured with the Frs2β (+/+) precancerous mammary cells, than with the Frs2β (−/−) cells (FIGS. 4F and 4G). CXCL12 binds to CXC receptor (CXCR) 4 and CXCR7. We did not observe significant effects on the mobilization of CAFs by treatment with the reported optimal concentration of the CXCR4 inhibitor AMD3100 (100 μg/ml) or Compound 1 (100 μg/ml) alone (data not shown); whereas, upon treatment with a combination of both the inhibitors, the mobilization of CAFs was greatly decreased in a dose dependent manner (FIGS. 4H, 4I). These findings suggest that CXCL12, derived from nearby Frs2β (+/+) precancerous mammary cells, plays an important role in the mobilization of CAFs. Therefore, it appears that the FRS2β-dependent increased production of cytokines, including IGF1 and CXCL12, in precancerous mammary cells allows the maintenance of CSCs and the mobilization of CAFs.

Figure 5A:
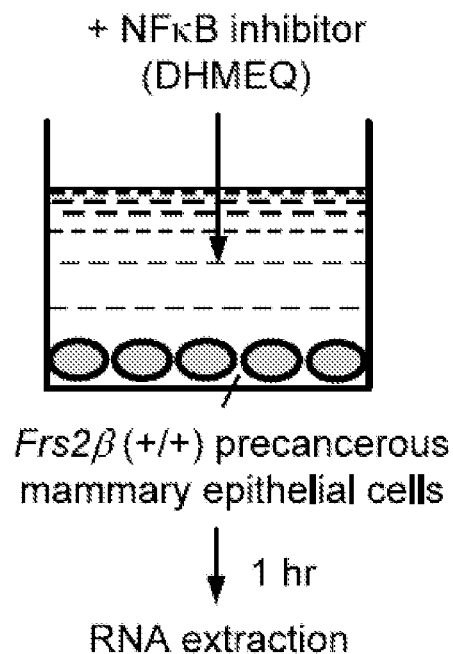
Figure 5B:
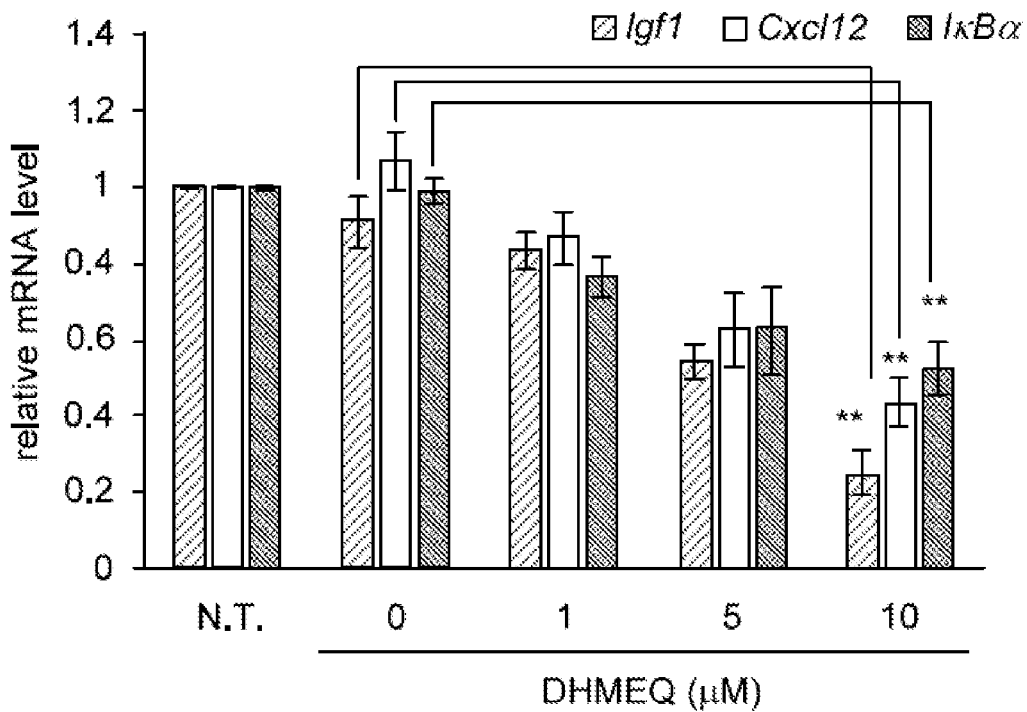

What are the molecular mechanisms that induce expression of IGF1 and CXCL2 in precancerous mammary tissues? Because Igf1 and Cxcl12 were included in the NFkB target gene set (FIG. 3D), and the AKT-NFkB axis is activated by many signaling pathways that include ErbB2 and CXCL12, we investigated whether activation of NFkB is involved in the production of these cytokines. To this end, we cultured Frs2β (+/+) precancerous mammary epithelial cells and treated them with DHMEQ, a specific inhibitor of NFkB (FIG. 5A). Treatment with DHMEQ inhibited the expression of Igf1, Cxcl12, and IkBa, a well-known NFkB-inducible gene, in a dose-dependent manner (FIG. 5B), suggesting that NFkB activation plays important roles in the expression of IGF1 and CXCL12 in precancerous mammary epithelial cells.

Figure 5C:
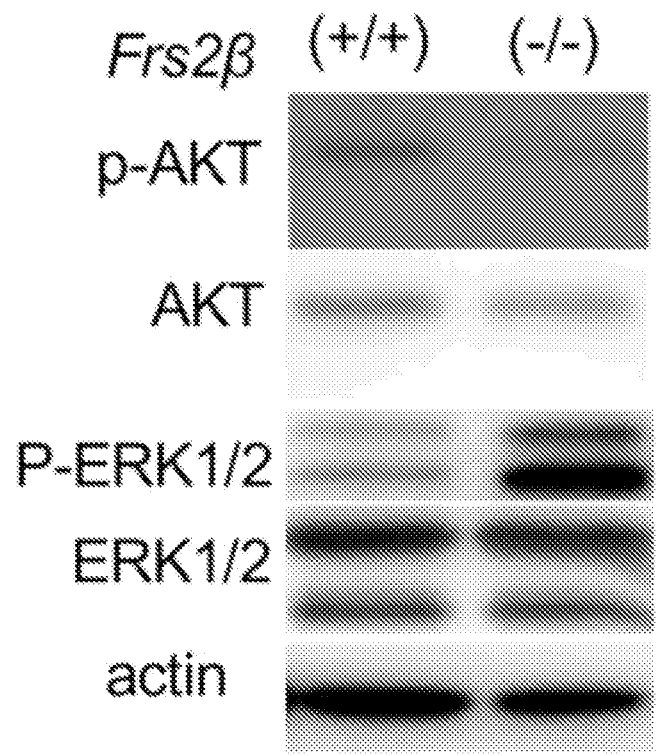
Figure 5D:
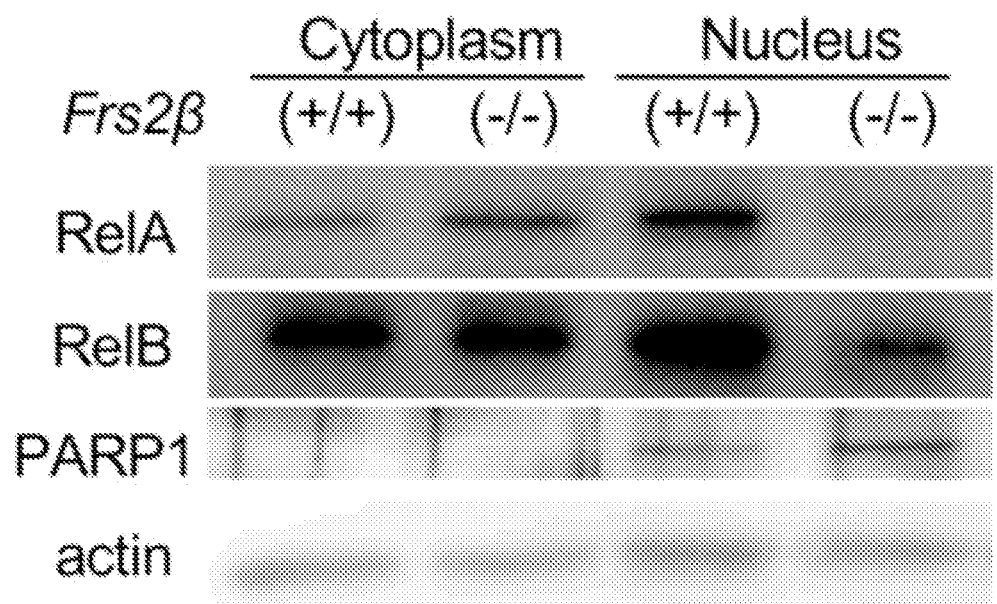
Figure 5E:
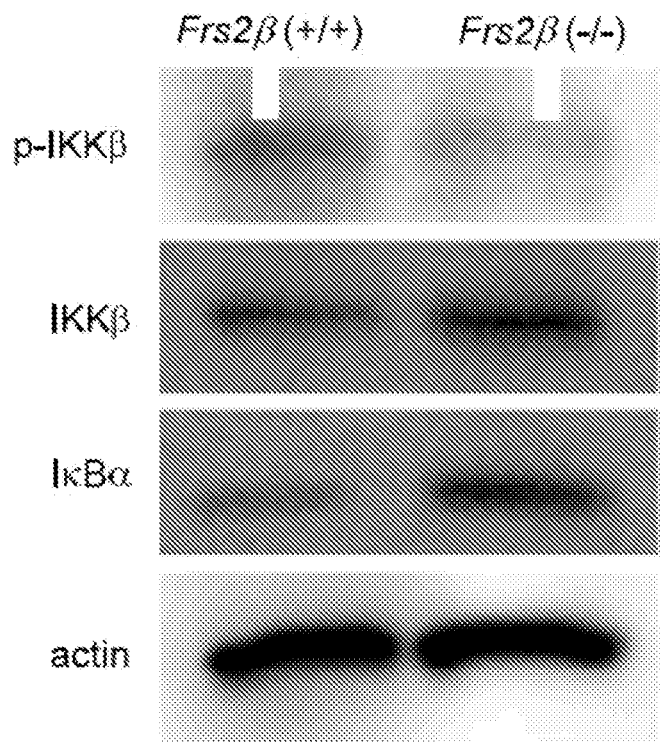
Figure 5F:
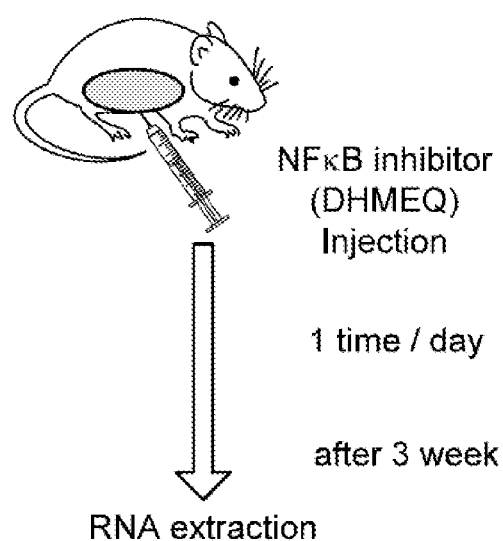
Figure 5G:
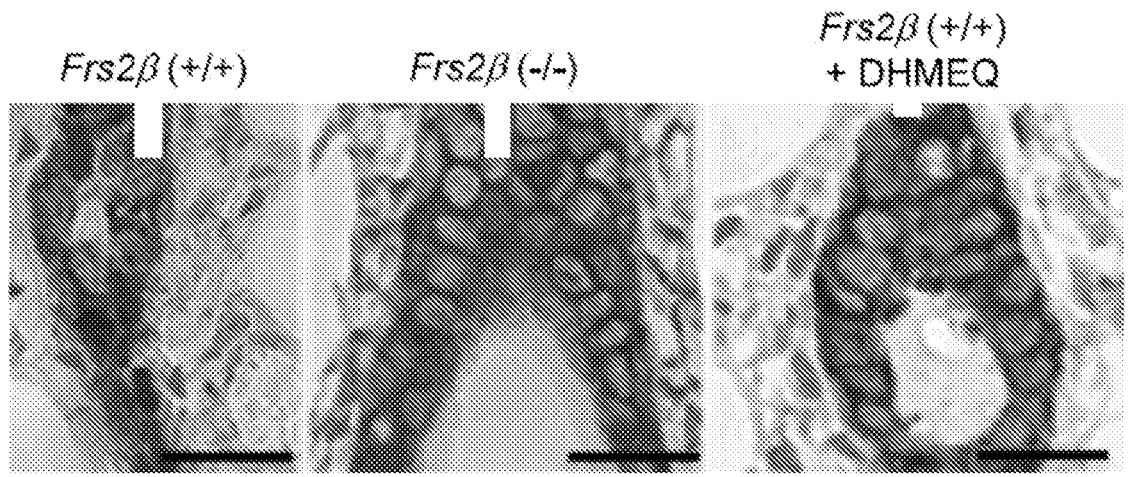
Figure 5H:
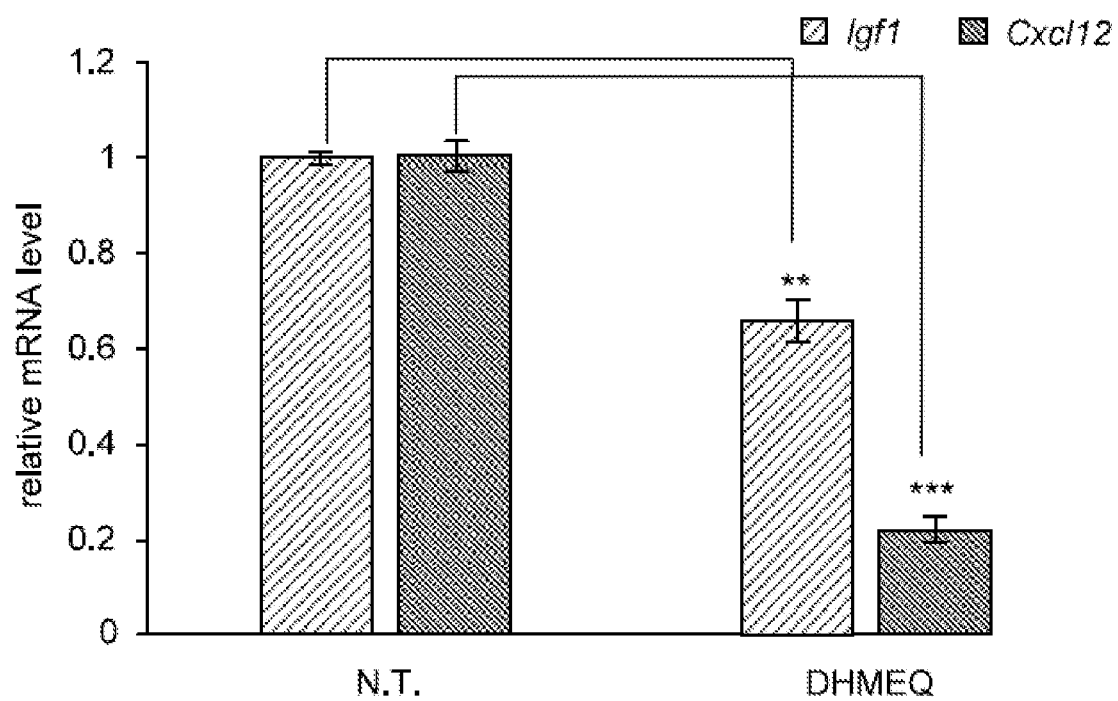

We next examined activation of the AKT-NFkB axis in precancerous mammary tissues in vivo. Immunoblotting of lysates from precancerous mammary tissues revealed a higher level of phosphorylated AKT, higher amounts of the NFkB components RelA and RelB in the nucleus, a higher level of phosphorylated IKKb, and a lower level of IkBa in Frs2β (+/+) tissues relative to Frs2β (−/−) tissues (FIG. 5C-5E). As expected, phosphorylated ERK1/2 was present at lower levels in Frs2β (+/+) tissues than in Frs2β (−/−) tissues (FIG. 5C). Moreover, immunohistochemistry revealed that RelA was localized to the nucleus in a much greater proportion of Frs2β (+/+) than Frs2β (−/−) precancerous luminal cells (FIG. 5G, red arrowheads in left panel and middle panel). Treatment with DHMEQ in vivo dramatically decreased the number of Frs2β (+/+) precancerous luminal cells harboring RelA in the nucleus (FIGS. 5F and G, right panel) and inhibited expression of Igf1 and Cxcl12 transcripts in precancerous mammary tissues (FIG. 5H). These results suggest that NFkB activation in precancerous luminal cells plays important roles in the expression of IGF1 and CXCL12 in precancerous mammary epithelial cells in vivo. It appears that FRS2β triggers the AKT-NFkB axis in the precancerous luminal cells, thereby inducing production of cytokines including IGF1 and CXCL12, which in turn activate NFkB in an autocrine or paracrine manner to spread the effects of activation of NFkB to the surrounding mammary epithelial cells.

Figure 5I:
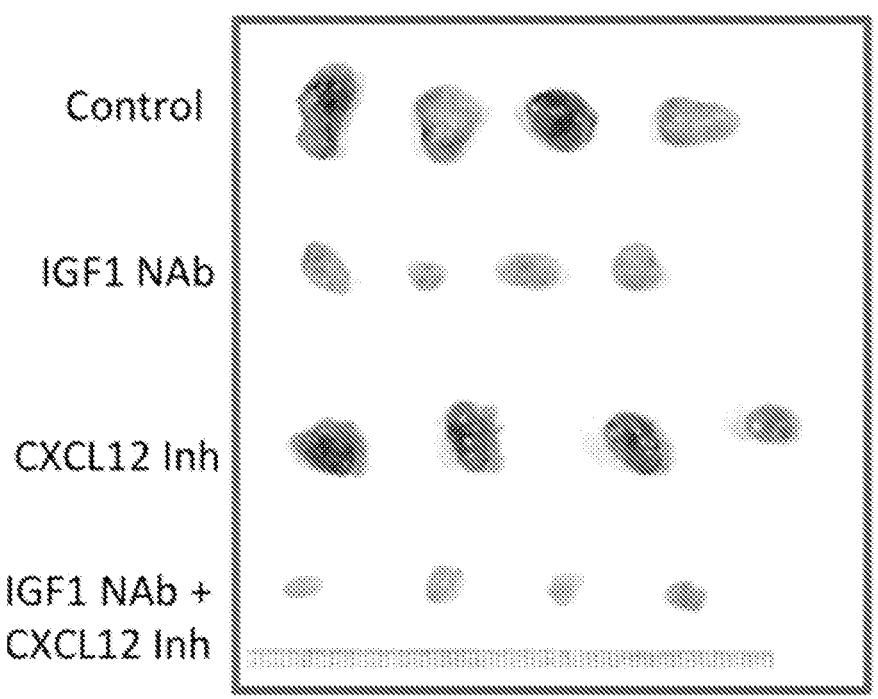
Figure 5J:
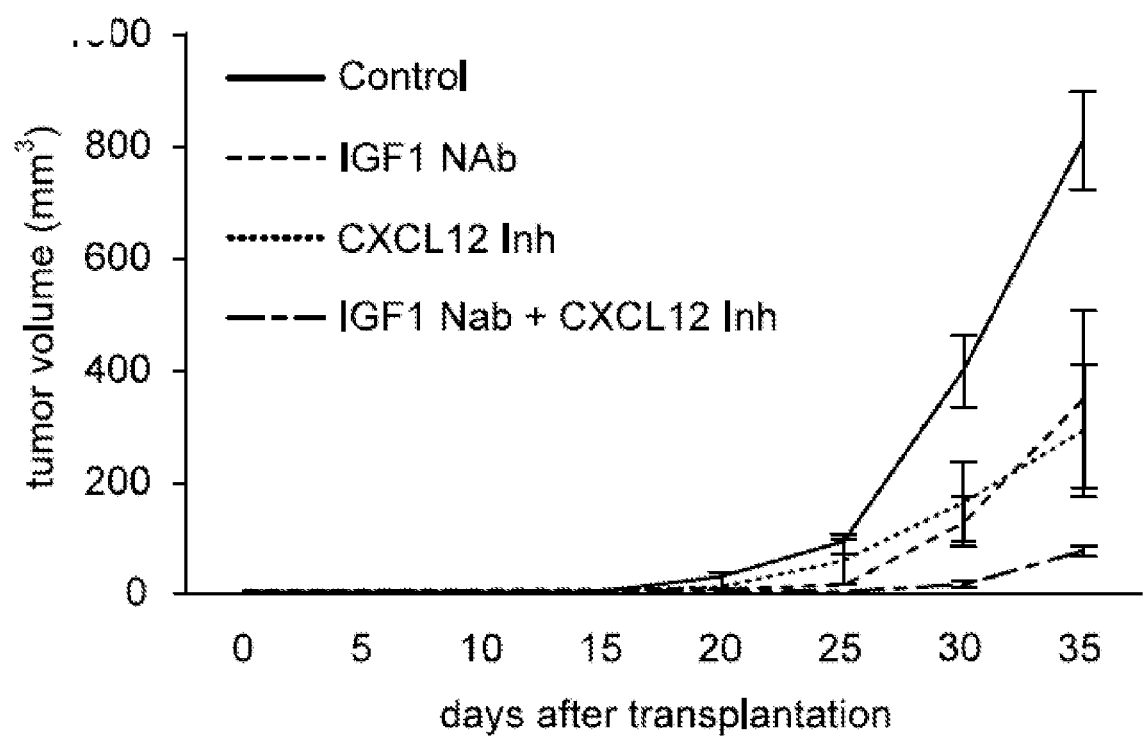
Figure 5K:
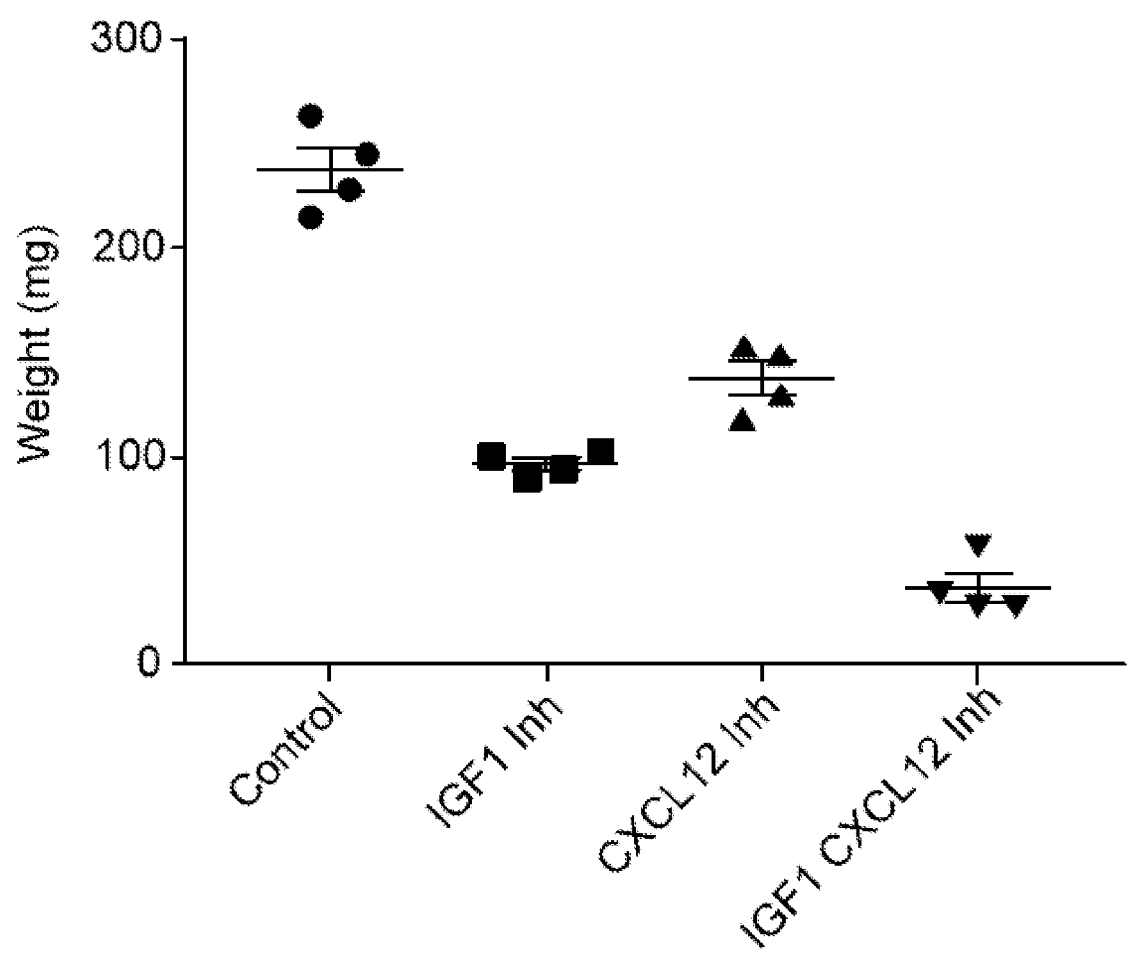

To examine whether IGF1 and CXCL12 expressed in the precancerous mammary microenvironment contribute to tumorigenesis, we treated the Frs2β (+/+) mice with the IGF1 neutralizing antibody and/or a combination of a CXCR4 inhibitor and a CXCR7 inhibitor (Compound 1) (both together, CXCL12 inhibitor) after inoculation of the Frs2β (+/+) tumor cells. Treatment with either the IGF1 neutralizing antibody or the CXC12 inhibitor significantly decreased the tumorigenesis and the combined treatment with both the IGF1 neutralizing antibody and the CXCL12 inhibitor showed the greatest inhibitory effect on tumor volumes and weights (FIG. 5I-5K). Body weights were not changed significantly (data not shown), indicating that there were no toxic effects. These results indicate that the FRS2β-dependent increased production of IGF1 and CXCL12 in the precancerous mammary tissues create the microenvironment that is essential for tumorigenesis.

Figure 6A:
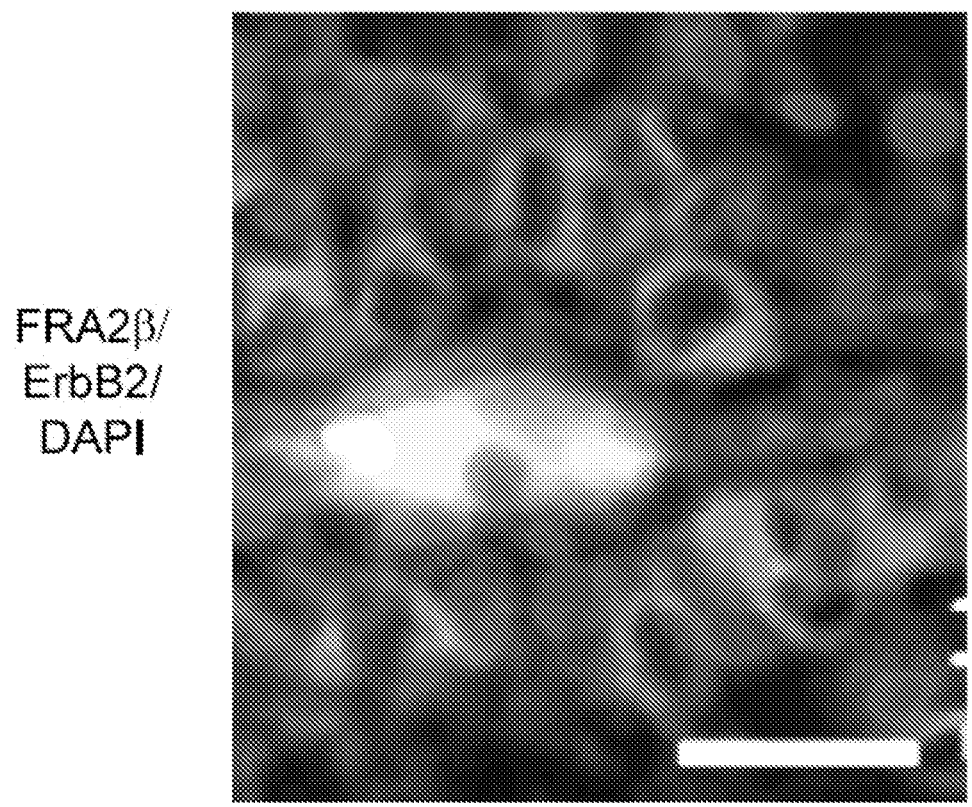
Figure 6B:
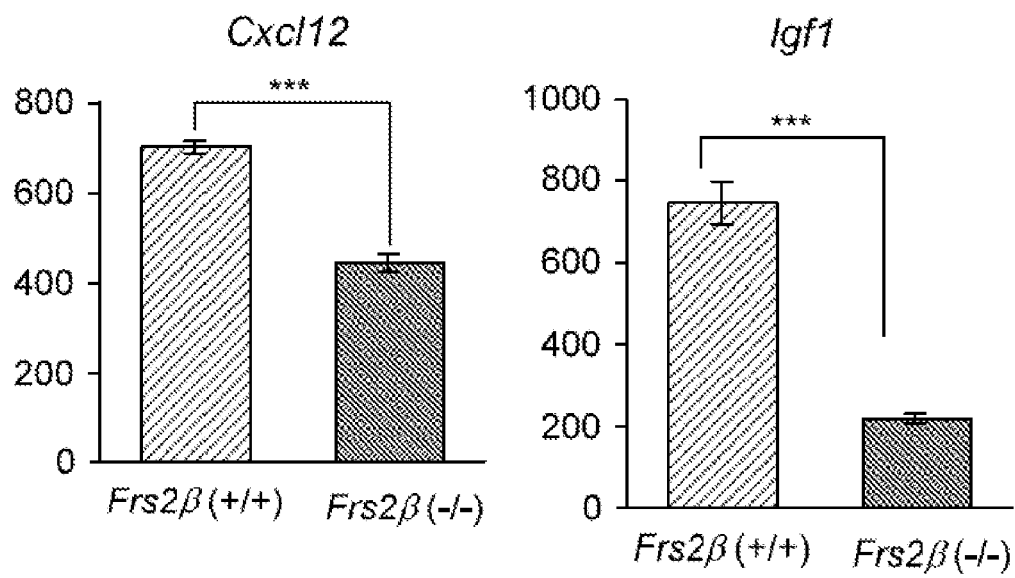
Figure 6C:
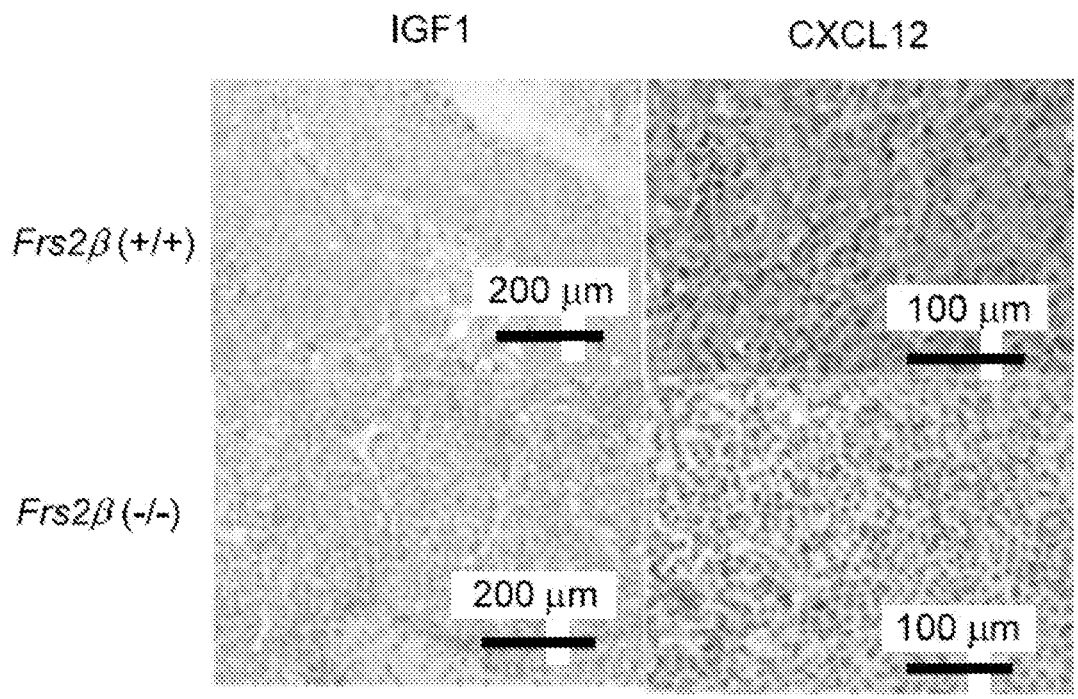

We next examined FRS2β expression in mammary tumors. Immunohistochemistry revealed that FRS2β-expressing cells were present in mammary tumors (FIG. 6A). Expression levels of Igf1 and Cxcl12 were higher in Frs2β (+/+) tumors than in Frs2β (−/−) tumors (FIG. 6B). Immunohistochemistry confirmed that expression levels of IGF1 and CXCL12 were higher in the Frs2β (+/+) tumors than in Frs2β (−/−) tumors (FIG. 6C). Therefore, it is reasonable to speculate that FRS2β triggers the AKT-NFkB axis to induce IGF1 and CXCL12 production in tumor tissues.

Figure 6D:
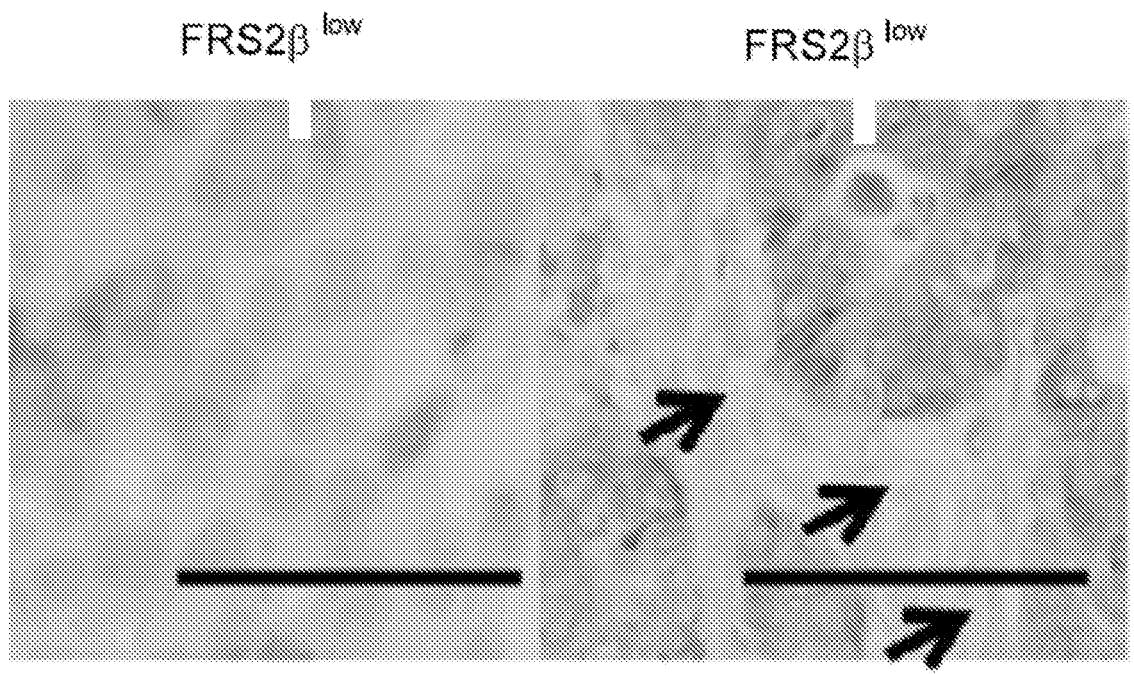
Figure 6E:
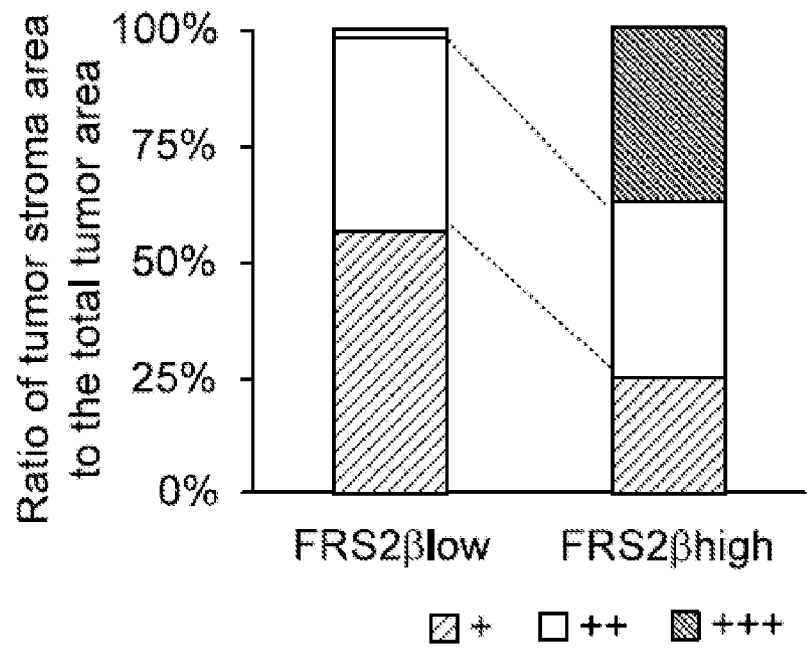
Figure 6F:
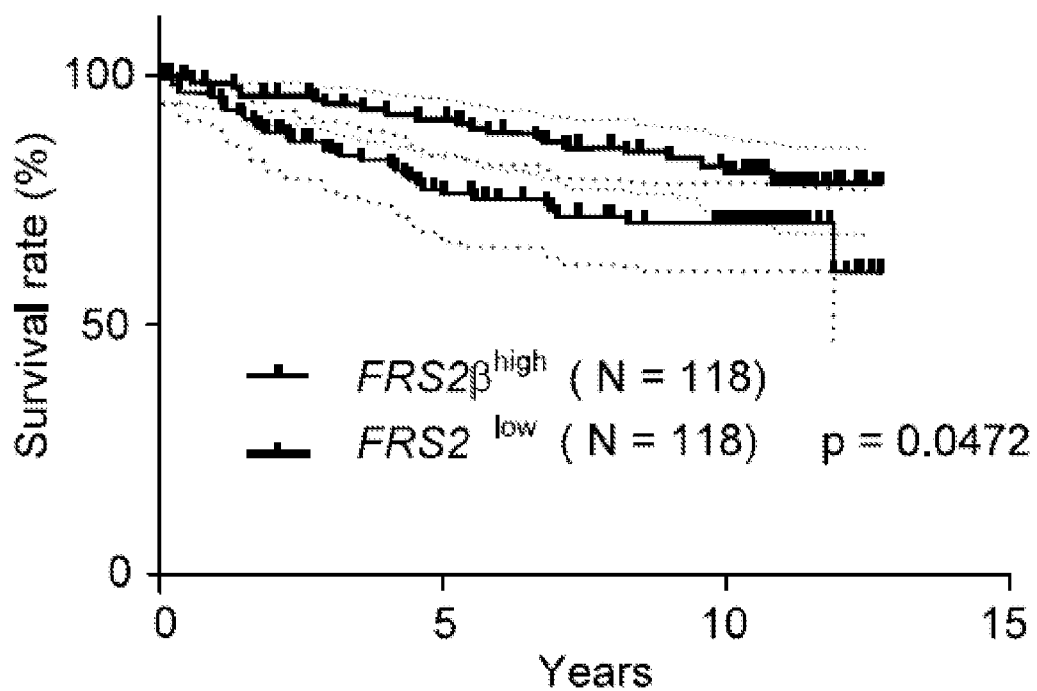

Finally, we examined the expression of FRS2β in human breast cancer tissues by immunohistochemistry. Expression levels of FRS2β varied among cancer cells (FIG. 6D). Breast cancer tissues in which FRS2β expression levels were high (+++) harbored significantly higher levels of cancer stroma than those with middle (++) or low (+) levels of FRS2β expression (p=0.0499, Barnard's test) (FIG. 6E). Furthermore, analysis of published gene expression profiles revealed that patients with higher expression levels of FRS2β in breast cancer tissues had a poorer prognosis (FIG. 6F).

Figure 6G:
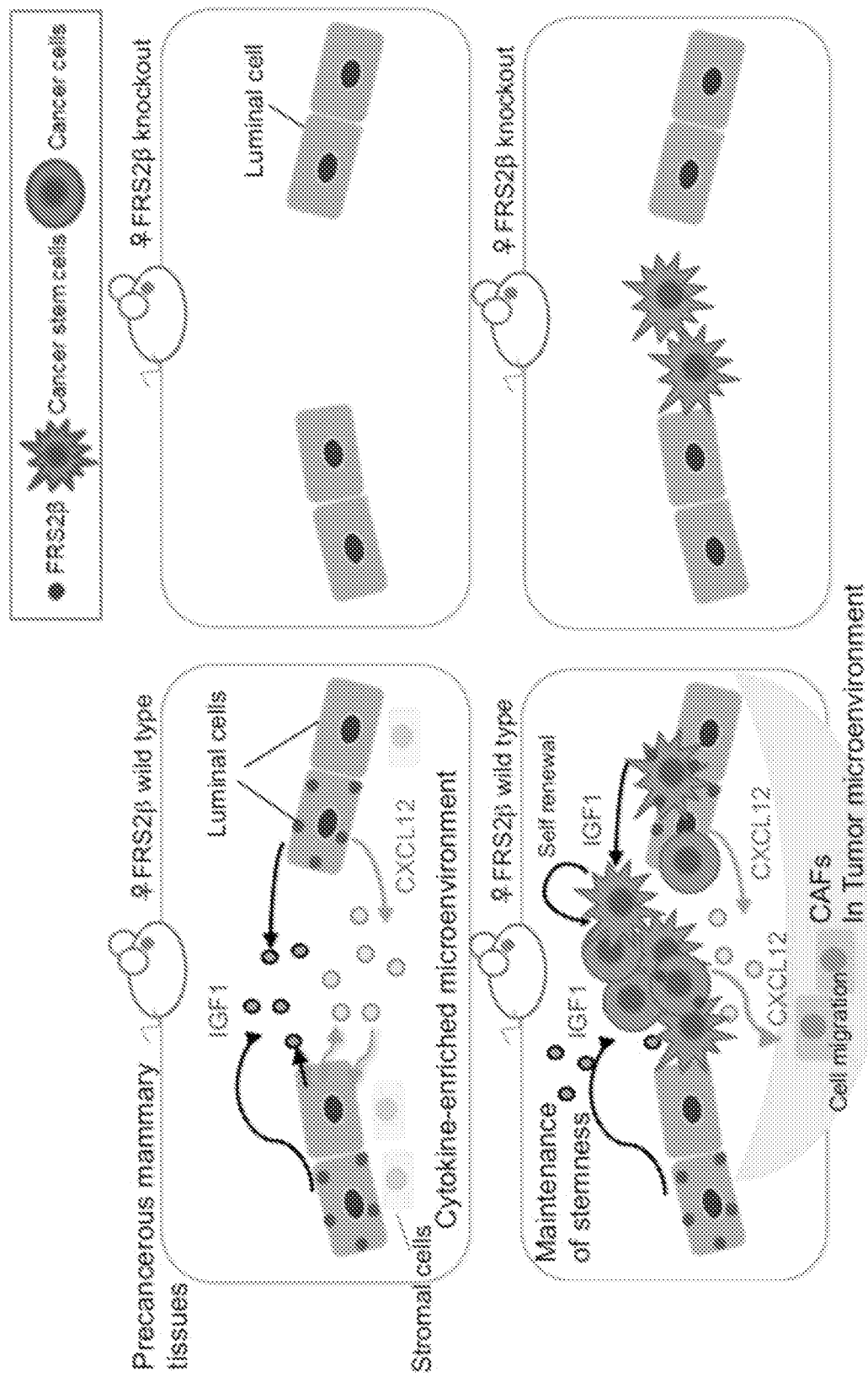

In this study, we demonstrated that FRS2β protein is expressed in a subset of luminal cells and triggers production of cytokines, including IGF1 and CXCL12. FRS2β may stimulate the AKT-NFkB axis to promote production of cytokines while inhibiting ERK signaling. It appears that these cytokines in turn activate NFkB in surrounding mammary luminal cells in an autocrine or paracrine manner, leading to creation of a cytokine-rich precancerous microenvironment that includes some amount of stroma prior to tumor onset (FIG. 6G, upper left panel). Once CSCs appear in the precancerous microenvironment, they may be able to self-renew in the presence of IGF1 and produce tumor cells with the help of CXCL12-mobilized stromal cells, which subsequently become CAFs. CSCs and tumor cells may produce IGF1 and CXCL12 on their own, leading to rapid growth and tumorigenesis (FIG. 6G, lower left panel). Without FRS2β, cytokines remain at low levels, and no appropriate precancerous microenvironment is created (FIG. 6G, upper right panel); even when CSCs appear, they cannot efficiently grow (FIG. 6G, lower right panel). Based on these findings, we propose that FRS2β is a promising target for prevention of breast cancer. In addition, we showed that combination therapy targeting IGF1 and CXCL12 effectively prevents tumorigenesis at the early stage.

The tumor microenvironment consists of various cell types: CAFs, mesenchymal stem cells, bone marrow-derived dendritic cells, immune cells, and newly formed blood vessels (3). On the other hand, it remains unclear which cell types in the precancerous microenvironment contribute to tumor onset. Here, we discovered that luminal cells and luminal progenitor cells are an important cell type in the precancerous microenvironment, and that FRS2β expressed in luminal cells and luminal progenitor cells plays critical roles in production of cytokines, leading to creation of the cytokine-rich precancerous microenvironment that is essential for tumor development.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of treating cancer in an individual in need thereof, said method comprising administering to the individual a CXCR7 inhibitor, wherein the individual has aberrant expression of FRS2β, and wherein the CXCR7 inhibitor has the structure of Formula I or Formula II:

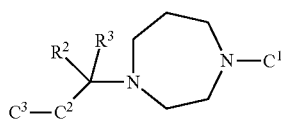
(I)

or a pharmaceutically acceptable salt thereof, wherein
$R^2$ and $R^3$ are each H,
$C^1$ is quinolinyl, which is optionally substituted with from 1 to 3 $R^4$ substituents;
$C^2$ is selected from the group consisting of thiazole, pyrazole, and oxazole, each of which is optionally substituted with from 1 to 2 $R^5$ substituents;
$C^3$ is selected from the group consisting of cyclohexyl, piperidinyl, and phenyl, wherein each of which is optionally substituted with from 1 to 2 $R^6$ substituents
each $R^4$ is independently selected from the group consisting of
methyl, ethyl, isopropyl, 2-fluoroethyl, 2-fluoroisopropyl, 2-hydroxyisopropyl, methoxy, chloro, —$CO_2H$, —$CH_2CO_2H$, X—$CO_2H$;
each $R^5$ is independently selected from the group consisting of methyl, fluoro, chloro, —$CO_2H$ and —$CH_2CO_2H$;
each $R^6$ is independently selected from the group consisting of methyl, fluoro, chloro, —OH, —$CO_2H$ and —$CH_2CO_2H$; and
each X is a linking group having the formula selected from the group consisting of —$OCH_2$—, —$OCH_2CH_2$—, —$OCH_2CH_2CH_2$—: or

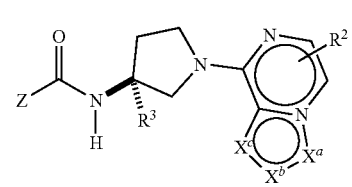
(II)

or a pharmaceutically acceptable salt thereof, wherein
the bicyclic portion having $X^a$, $X^b$ and $X^c$ as ring vertices is selected from:

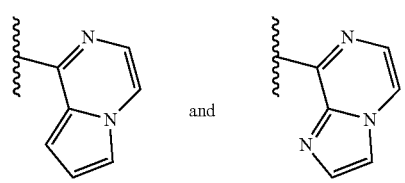 [SMILES: *c1nccn2cccc12 ; *c1nccn2ccnc12]

$R^2$ is selected from the group consisting of H and $C_{1-8}$ alkyl;
$R^3$ is hydrogen;
Z is

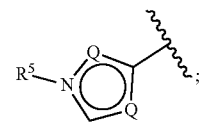

each Q is N;
$R^5$ is aryl optionally further substituted with 1-3 $R^a$; and
each $R^a$ is halogen or $C_{1-8}$ alkyl.

2. The method of claim 1, wherein the CXCR7 inhibitor has the structure selected from the group consisting of (Compound 1), (Compound 2), (Compound 3), (Compound 4), (Compound 5), (Compound 6), (Compound 7), (Compound 8), (Compound 9)

or a pharmaceutically acceptable salt thereof.

3. The method of claim 1, wherein the cancer is selected from the group consisting of breast cancer, uterine cancer, ovarian cancer, cervical cancer, stomach cancer, pancreatic cancer, rectal cancer, kidney cancer, renal cancer, bladder cancer, prostate cancer, and adrenal cancer.

4. The method of claim 1, wherein the cancer is breast cancer.

5. The method of claim 1, wherein the individual expresses FRS2β in one or more luminal progenitor cells.

6. The method of claim 1, wherein the individual expresses FRS2β in one or more mammary luminal progenitor cells.

7. The method of claim 1, further comprising administering an additional therapeutic agent.

8. The method of claim 1, further comprising administering therapeutically effective amounts of an anti-IGF1 antibody and a CXCR4 inhibitor.

9. The method of claim 1, further comprising administering a therapeutically effective amount of an anti-IGF1 antibody.

10. The method of claim 1, further comprising administering a therapeutically effective amount of a CXCR4 inhibitor.

11. The method of claim 1, wherein prior to administration of a CXCR7 inhibitor or an additional therapeutic agent the individual was diagnosed with having aberrant expression of FRS2β.

12. A method of treating breast cancer in an individual in need thereof, said method comprising administering to a subject in need thereof a compound selected from the group consisting of (Compound 1)

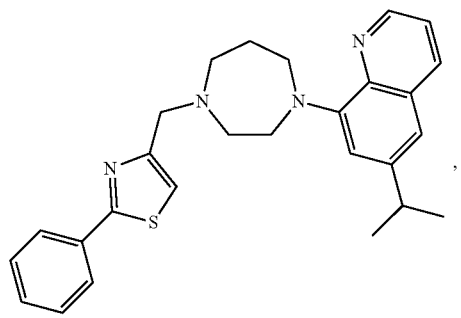

(Compound 2)

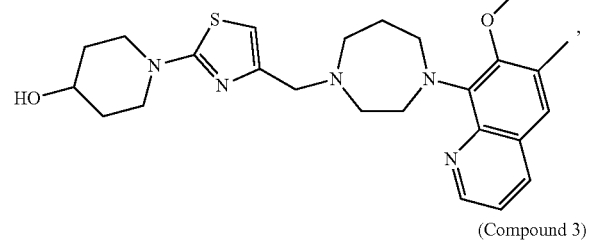

(Compound 3)

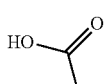

(Compound 4)

(Compound 5)

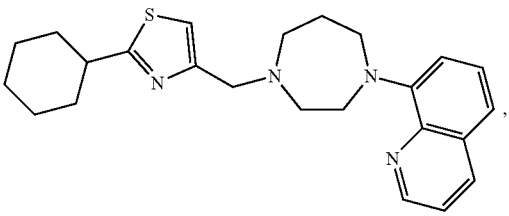

(Compound 6)

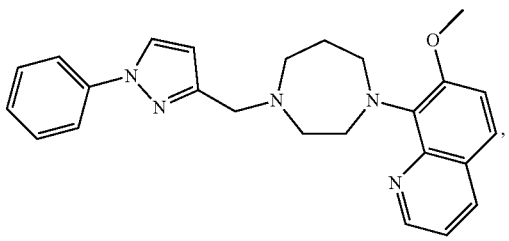

(Compound 7)

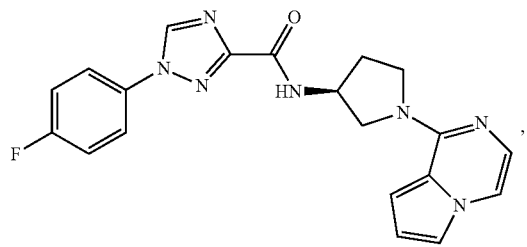

(Compound 8)

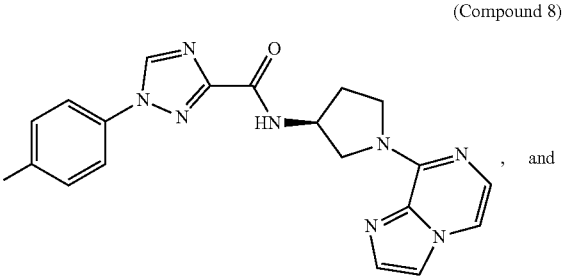, and (Compound 9)

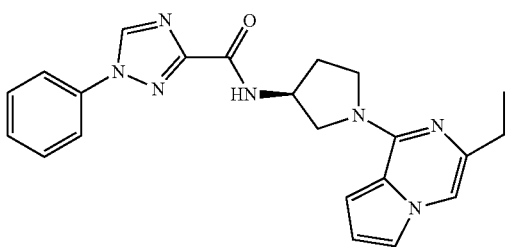

or a pharmaceutically acceptable salt thereof.

13. The method of claim 12, wherein prior to administration the individual has been diagnosed as having aberrant expression of FRS2β.

14. The method of claim 12, further comprising administering an additional therapeutic agent.

15. The method of claim 12, wherein the compound is (Compound 1)

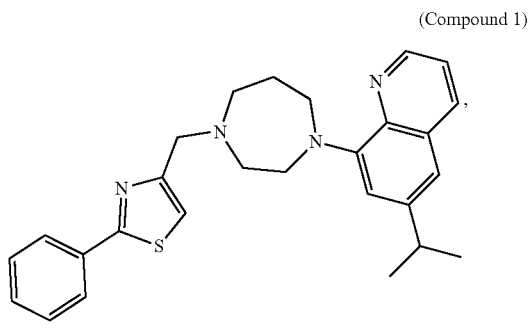 [SMILES: CC(C)c1cc(N2CCCN(Cc3csc(-c4ccccc4)n3)CC2)c2ncccc2c1]

or a pharmaceutically acceptable salt thereof.

16. The method of claim 12, wherein the compound is (Compound 2)

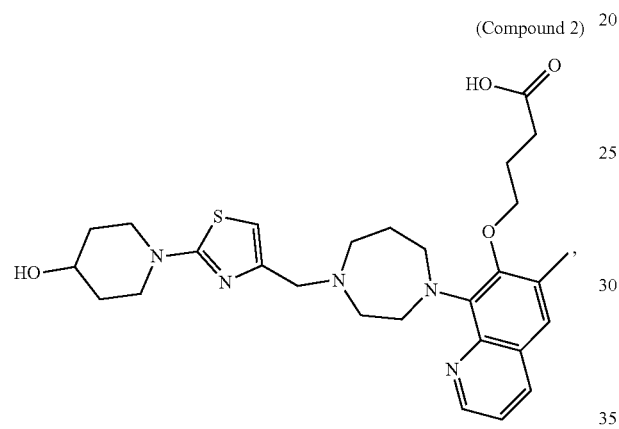

or a pharmaceutically acceptable salt thereof.

17. The method of claim 12, wherein the compound is (Compound 3)

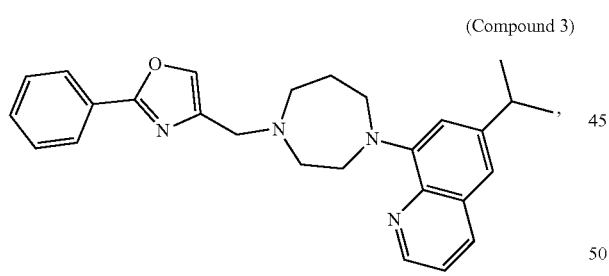

or a pharmaceutically acceptable salt thereof.

18. The method of claim 12, wherein the compound is (Compound 4)

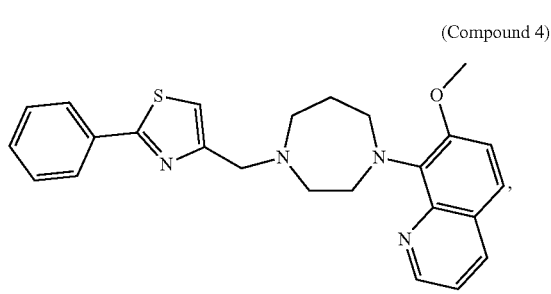 [SMILES: COc1ccc2cccnc2c1N1CCCN(Cc2csc(-c3ccccc3)n2)CC1]

or a pharmaceutically acceptable salt thereof.

19. The method of claim 12, wherein the compound is (Compound 5)

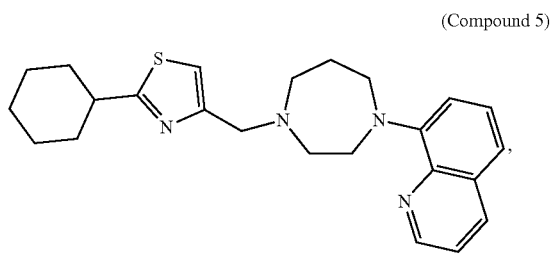 [SMILES: c1cnc2c(N3CCCN(Cc4csc(C5CCCCC5)n4)CC3)cccc2c1]

or a pharmaceutically acceptable salt thereof.

20. The method of claim 12, wherein the compound is (Compound 6)

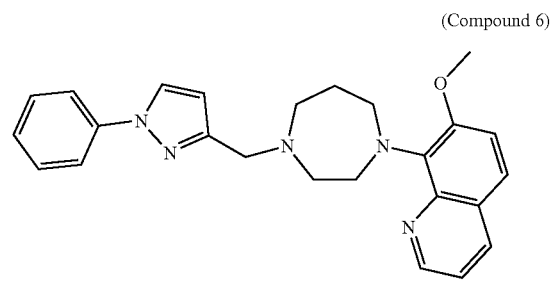 [SMILES: COc1ccc2cccnc2c1N1CCCN(Cc2ccn(-c3ccccc3)n2)CC1]

or a pharmaceutically acceptable salt thereof.

* * * * *